US009872925B2

(12) United States Patent
Chung et al.

(10) Patent No.: US 9,872,925 B2
(45) Date of Patent: Jan. 23, 2018

(54) VITAMIN B6-COUPLED POLY(ESTER AMINE) AS GENE CARRIER AND APPLICATION IN CANCER GENE THERAPY

(71) Applicant: SNU R&DB FOUNDATION, Seoul (KR)

(72) Inventors: Jong Hoon Chung, Seoul (KR); Shambhavi Pandey, Seoul (KR); Pankaj Garg, Seoul (KR); Pill Hoon Choung, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/182,031

(22) Filed: Feb. 17, 2014

(65) Prior Publication Data

US 2015/0030854 A1     Jan. 29, 2015

(30) Foreign Application Priority Data

Jul. 26, 2013   (KR) .................. 10-2013-0089145

(51) Int. Cl.
| | |
|---|---|
| *A61K 48/00* | (2006.01) |
| *C12N 15/11* | (2006.01) |
| *C12N 15/113* | (2010.01) |
| *A61K 47/55* | (2017.01) |
| *A61K 47/59* | (2017.01) |
| *A61K 47/69* | (2017.01) |

(52) U.S. Cl.
CPC ........ *A61K 48/0075* (2013.01); *A61K 47/551* (2017.08); *A61K 47/59* (2017.08); *A61K 47/6921* (2017.08); *A61K 48/0041* (2013.01); *C12N 15/111* (2013.01); *C12N 15/1137* (2013.01); *C12Y 201/02001* (2013.01); *C12N 2310/14* (2013.01); *C12N 2310/351* (2013.01); *C12N 2320/32* (2013.01); *Y10T 428/2982* (2015.01)

(58) Field of Classification Search
None
See application file for complete search history.

(56) References Cited

U.S. PATENT DOCUMENTS

2007/0092558 A1* 4/2007 Heavner ................ A61K 9/127
424/450

FOREIGN PATENT DOCUMENTS

KR    1020100001563    *  1/2010    ............. C08G 63/68

OTHER PUBLICATIONS

Rao et al., Molecular organization, catalytic mechanism and function of serine hydroxymethyltransferase—a potential target for cancer chemotherapy; Intl J Biochem and Cell Biol., vol. 32, pp. 405-416, 2000.*
Schiffelers et al., Cancer siRNA therapy by tumor selective delivery with ligand-targeted sterically stabilized nanoparticle; NAR, vol. 32, No. 19, e149: 10 pages, 2004.*
Cho et al., Korean Patent Application Publication No. 1020100001563, Jan. 6, 2010; Original text and Machine translation, accessed Sep. 9, 2015; 15 pages.*

* cited by examiner

*Primary Examiner* — Addison D Ault
(74) *Attorney, Agent, or Firm* — Gavrilovich, Dodd & Lindsey LLP

(57) ABSTRACT

The present invention relates to a vitamin B6-coupled poly (ester amine) (VBPEA) as a gene carrier and a method for preparing the gene carrier. Moreover, the present invention relates to a gene delivery complex comprising a therapeutic gene coupled to the gene carrier and a pharmaceutical formulation for gene therapy, which comprises the gene delivery complex as an active ingredient. In addition, the present invention relates to gene therapy utilizing the gene carrier, the gene delivery complex or the pharmaceutical formulation. The VBPEA of the invention has a significantly high gene delivery rate compared to existing gene carriers and a complex of the VBPEA with DNA has little or no cytotoxicity and shows a very high in vivo transfection efficiency. In addition, a complex of the VBPEA with siRNA shows high gene silencing efficiency and can induce a high rate of cell death and the inhibition of cell proliferation in cancer cells, suggesting that it can be used for anticancer gene therapy. Thus, the gene carrier VBPEA of the invention can be used as an experimental gene carrier and can also be widely used in gene therapy against various diseases depending on the kind of therapeutic gene.

7 Claims, 25 Drawing Sheets

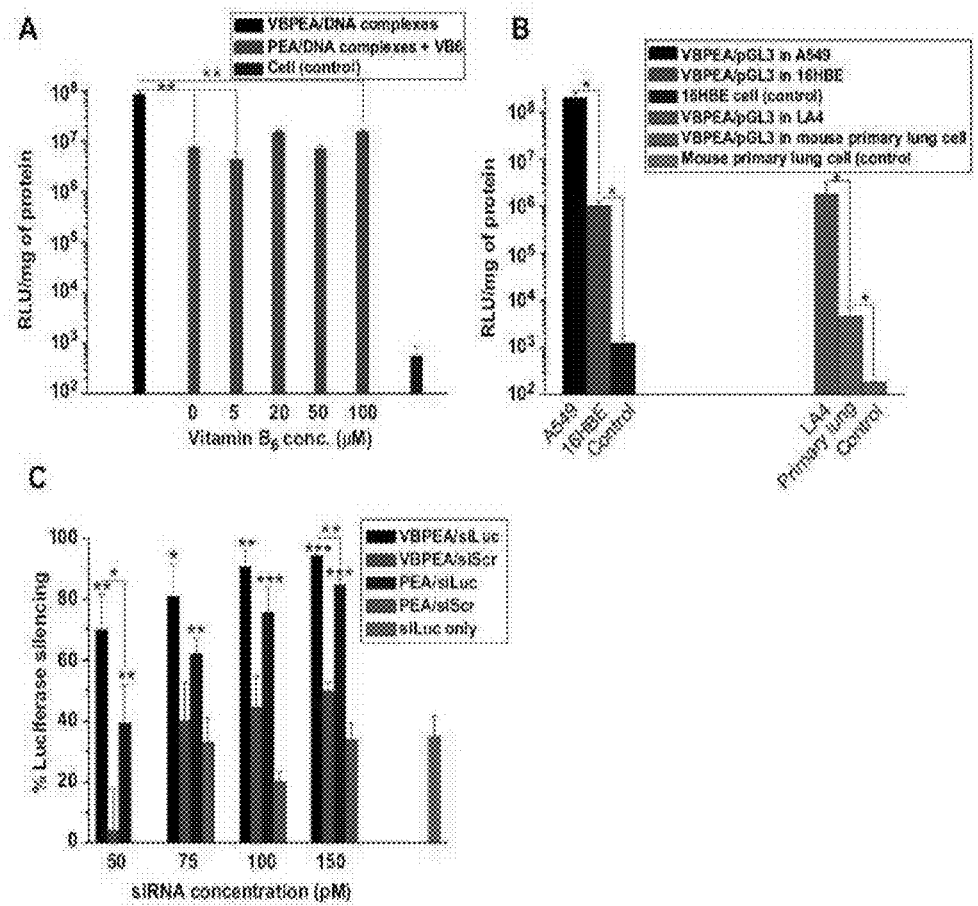
FIGURE 7A-C

VITAMIN B6-COUPLED POLY(ESTER AMINE) AS GENE CARRIER AND APPLICATION IN CANCER GENE THERAPY

CROSS REFERENCE TO RELATED APPLICATIONS

This application claims priority to Korean Application No. 10-2013-0089145, filed Jul. 26, 2013, the disclosure of which is incorporated herein by reference.

TECHNICAL FIELD

The present invention relates to a vitamin B6-coupled poly(ester amine) (VBPEA) as a gene carrier and a method for preparing the gene carrier. Moreover, the present invention relates to a gene delivery complex comprising a therapeutic gene coupled to the gene carrier and a pharmaceutical formulation for gene therapy, which comprises the gene delivery complex as an active ingredient. In addition, the present invention relates to gene therapy utilizing the gene carrier, the gene delivery complex or the pharmaceutical formulation.

BACKGROUND

Gene therapy is a method in which a therapeutic gene is delivered to a target organ in vivo so that a new protein is expressed in cells to treat disease. It is not a method of treating the symptoms of disease, but is a method of treating by removing the cause of the disease. Gene therapy may have high selectivity compared to treatment with general drugs and improve the cure rate of disease difficult to control by other therapeutic methods, and thus it can be applied for a long period of time. DNA, a therapeutic gene, is susceptible to hydrolysis by enzymes in vivo and introduced into cells with low efficiency. For this reason, for effective gene therapy, it is required to develop a gene carrier that can safely deliver a therapeutic gene to a target cell to achieve high expression efficiency.

Gene carriers should have low or no toxicity and should be capable to deliver a therapeutic gene to a target cell in a selective and effective manner. Such gene carriers can be largely divided into viral gene carriers and non-viral gene carriers. So far, in clinical trials, viral vectors having high transfection efficiency have been used as gene carriers. However, viral vectors such as retrovirus, adenovirus or adeno-associated virus have problems in that they are prepared by complex processes and pose safety-related concerns, including immunogenicity, infection possibility, proinflammatory potential, and non-specific insertion of DNA and in that the size of DNA capable of being received therein is limited. Due to such problems, the application of such gene carrier to the human body is significantly limited. For this reason, non-viral vectors are receiving attention as an alternative to viral vectors.

Non-viral vectors have advantages in that they can be repeatedly administered with minimal immune responses, can be delivered specifically to a target cell, have excellent storage stability, and are easily produced in large amounts. Examples of such non-viral vectors include cationic liposomes such as N-[1-(2,3-dioleyloxy)propyl]-N,N,N-trimethylammonium chloride (DOTMA), alkylammonium, cationic cholesterol derivatives, gramicidin and the like.

In recent years, cationic polymers among non-viral vectors have received a lot of attention, because they can complexes by ionic bonding with negatively charged DNA. Such cationic polymers include poly-L-lysine (PLL), poly (4-hydroxy-L-proline ester), polyethyleneimine (PEI), poly [α-(4-aminobutyl)-L-glycolic acid], polyamidoamine dendrimers, poly[N,N'-(dimethylamino)ethyl]methacrylate (PDMAEMA) and the like. These cationic polymers can condense DNA to form nanoparticles to thereby protect DNA from enzymatic degradation, and allow DNA to penetrate rapidly into cells and to be released from endosomes. Most non-viral vectors have advantages over viral vectors, including biodegradability, low toxicity, non-immunogenicity, and convenience in use, but have problems, including relatively low transfection efficiency, limited particle size, and the like.

Particularly, most cationic polymers that are used as non-viral vectors show high transfection efficiency in an in vitro environment having low serum concentration, but have problems in that the efficiency of transfection of cationic polymer/gene complexes is significantly reduced by various factors present in serum in an in vivo environment so that the introduction of the gene into cells is not smooth. This is because excessive positive charges occur on the surface of cationic polymer/gene complexes in vivo to cause non-specific interactions with plasma proteins and blood constituents. Thus, in an in vivo environment in which a large amount of serum exists, as opposed to a serum-free medium in vitro or an environment in which serum exists at a very low concentration, the transfection efficiency of cationic polymers is significantly reduced. If these cationic polymers are applied in vivo, they can be agglomerated and accumulated in the lung, liver and spleen and opsonized and removed by the reticuoendothelial system. Thus, the therapeutic application of these cationic polymers can be greatly limited. Polyethyleneimine (PEI) that has been most extensively studied as a non-viral vector has also problems, including low in vivo transfection efficiency, high cytotoxicity, and a low gene expression effect due to low blood compatibility. Accordingly, there is an urgent need to develop a gene carrier which has enhanced transfection efficiency while maintaining the advantages of existing non-viral vectors.

Meanwhile, vitamin B6 (VB6) is a coenzyme that is involved in various cellular metabolisms, including DNA biosynthesis essential for the growth or proliferation of cells. VB6 is taken up by cells through facilitated diffusion via VB6 transporting membrane carrier (VTC) present on the cell membrane. Particularly, because the growth and proliferation of cancer cells actively occur, cancer cells require a large amount of vitamin B6 compared to general adult cells.

Accordingly, the present inventors have made extensive efforts to develop a gene carrier, which has low cytotoxicity, shows high transfection efficiency and can deliver a gene specifically to cancer cells. As a result, the present inventors have developed a vitamin B6-coupled poly(ester amine) gene carrier and have found that the gene carrier shows high transfection efficiency by increasing the accessibility of a complex of a gene and the gene carrier to the cell membrane using vitamin B6 receptors present on the cell membrane, thereby completing the present invention.

DISCLOSURE

Technical Problem

Therefore, it is an object of the present invention to provide a vitamin B6-coupled poly(ester amine) (VBPEA)

as a gene carrier, which has significantly increased transfection efficiency while showing no cytotoxicity.

Another object of the present invention is to provide a method for preparing the vitamin B6-coupled poly(ester amine).

Still another object of the present invention is to provide a gene delivery complex composed of a therapeutic gene coupled to the vitamin B6-coupled poly(ester amine).

Yet another object of the present invention is to provide a pharmaceutical formulation for gene therapy, which comprises the gene delivery complex as an active ingredient.

Technical Solution

In order to accomplish the above objects, in one aspect, the present invention provides a vitamin B6-coupled poly(ester amine) (VBPEA) represented by the following formula 1, for use as a gene carrier:

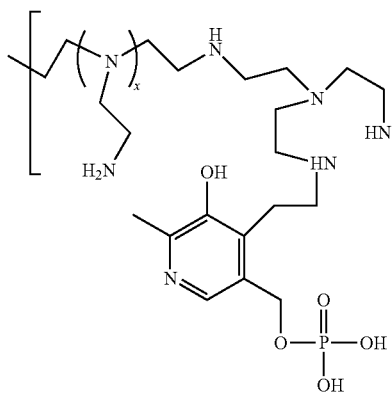

Formula 2

Formula 3

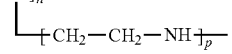

As used herein, the term "glycerol dimethacrylate (GDM)" refers to a glycerol derivative that is obtained as a byproduct of biodiesel production and is a human-friendly material that is frequently used as a contact lens material due to its high wettability. The glycerol dimethacrylate in the present invention may have a structure of the following formula 4:

Formula 1

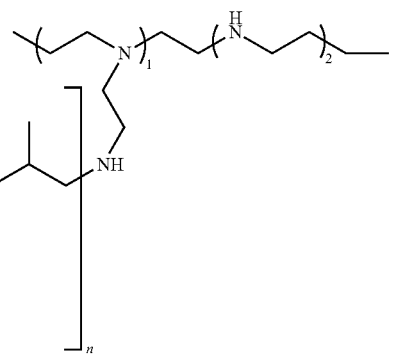

wherein n is an integer between 1 and 500. In the above formula, the red portion corresponds to a polyethyleneimine-derived moiety, the blue portion corresponds to a glycerol dimethacrylate-derived moiety, and the green portion corresponds to a vitamin B6-derived moiety.

The vitamin B6-coupled poly(ester amine) (VBPEA) can be prepared by preparing poly(ester-amine) (PEA) by the Michael addition reaction between low-molecular-weight polyethyleneimine (PEI) and glycerol dimethacrylate (GDM) and reacting the prepared poly(ester-amine) with activated vitamin B6 (pyridoxal 5'-phosphate, PLP).

As used herein, the term "polyethyleneimine (PEI)" refers to a cationic polymer having primary, secondary and tertiary amino groups and a molar mass of 1,000 to 100,000 g/mol. It can effectively condense a negatively charged gene to form colloidal particles and has high gene delivery efficiency due to its ability to buffer pH, and thus it can effectively deliver a gene to various cells in vitro and in vivo. The polyethyleneimine in the present invention may be a linear compound represented by the following formula 2 or a branched-type compound represented by the following formula 3 and has a weight-average molecular weight of 50-10,000 Da, and preferably 50-10,000 Da, in view of cytotoxicity. The polyethyleneimine dissolves in water, alcohol, glycol, dimethylformamide, tetrahydrofuran, esters and the like, and does not dissolve in high-molecular-weight hydrocarbons, oleic acid, diethylether or the like.

Formula 4

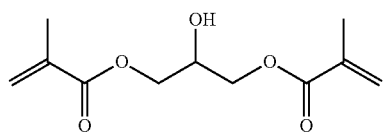

In the present invention, polyethyleneimine and glycerol dimethacrylate form poly(ester amine) (PEA) by the Michael addition reaction. It is known that poly(ester amine) itself can be used as a gene carrier. This is because of a cationic polyethyleneimine moiety having the capability to condense an anionic gene. Meanwhile, there has been a continued demand for a gene carrier having low cytotoxicity and high transfection efficiency compared to poly(ester amine), and particularly, there has been a continued demand for a gene carrier having high transfection efficiency for specific cells (e.g., cancer cells).

In the present invention, "vitamin B6" exists as pyridoxine (PN), pyridoxal (PL), pyridoxamine (PM), or their phosphate forms (PNP, PLP, and PMP), and is used as a coenzyme for various bioactive enzymes. Particularly, it is known that PLP and PMP are used as coenzymes and PLP has a very high biological activity. Activated vitamin B6 (pyridoxal 5'-phosphate; PLP) in the present invention may have a structure of the following formula 5:

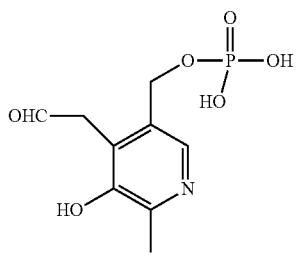

Formula 5

In the present invention, pyridoxal 5'-phosphate (PLP) is reacted with the prepared poly(ester amine) to form a transient Schiff base. Then, the Schiff base is reduced with NaCNBH$_4$ to obtain vitamin a B6-coupled poly(ester amine) (VBPEA) as a gene carrier.

As used herein, the term "vitamin B6-coupled poly(ester amine) (VBPEA)" refers to the compound represented by formula 1. Particularly, it may be a compound formed by preparing poly(ester amine) (PEA) by the Michael addition reaction between low-molecular-weight polyethyleneimine (LW PEI) and glycerol dimethacrylate (GDM) and reacting the prepared poly(ester amine) with activated vitamin B6 (pyridoxal 5'-phosphate).

The vitamin B6 in the vitamin B6-coupled poly(ester amine) (VBPEA) gene carrier of the present invention functions to bind to vitamin B6 transporter on the cell membrane to induce the adhesion of the gene carrier to the cell membrane, and after adhesion to the cell membrane, the internalization of the gene into cells is efficiently induced by the proton sponge effect of the poly(ester amine) (PEA) backbone. Thus, the vitamin B6-coupled poly(ester amine) (VBPEA) gene carrier can show a significantly increased transfection efficiency. In addition, it has a very low cytotoxicity, and thus can be effectively used as a gene carrier in gene therapy. Particularly, it can show high transfection efficiency for cancer cells requiring a large amount of vitamin B6, compared to normal cells.

The vitamin B6-coupled poly(ester amine) (VBPEA) gene carrier of the present invention preferably has a weight-average molecular weight of 1,000 to 100,000 Da for effective gene delivery. In addition, the gene delivery complex composed of a gene coupled to the vitamin B6-coupled poly(ester amine) (VBPEA) gene carrier of the present invention preferably has a zeta potential of 1-100 mV for effective gene delivery. Particularly, it may have a zeta potential of 25-50 mV. When the vitamin B6-coupled poly (ester amine) (VBPEA) gene carrier shows physiochemical properties within the above-described ranges, it can be effectively internalized into intracellular endosomes.

In one aspect, the present invention provides a method for preparing the vitamin B6-coupled poly(ester amine) (VBPEA) gene carrier, the method comprising the steps of: forming poly(ester amine) by the Michael addition reaction between low-molecular-weight polyethyleneimine and glycerol dimethacrylate; and reacting the formed poly(ester amine) with activated vitamin B6.

The method for preparing the vitamin B6-coupled poly (ester amine) (VBPEA) gene carrier according to the present invention may comprise the steps of:

a) adding a solution of low-molecular-weight polyethyleneimine (PEI) to a solution of glycerol dimethacrylate and subjecting the mixture solution to the Michael addition reaction; and b) separating poly(ester amine) (PEA) from the reaction product of step a);

c) reacting the separated poly(ester amine) of step b) with activated vitamin B6 (pyridoxal 5'-phosphate (PLP); and d) reducing the reaction product of step c) with NaCNBH$_4$ to obtain the vitamin B6-coupled poly(ester amine) (VBPEA) gene carrier.

In step a), the polyethyleneimine solution is added to the glycerol dimethacrylate solution with stirring, and the Michael addition reaction between polyethyleneimine and glycerol dimethacrylate is performed. In the present invention, the Michael addition reaction may be carried out at 40~100° C. for 1-72 hours. In the Michael addition reaction according to the present invention, the stoichiometric ratio of polyethyleneimine:glycerol dimethacrylate is 1:0.1 to 1:10, and preferably 1:0.5. In a preferred example of the present invention, the polyethyleneimine solution was slowly added dropwise to the glycerol dimethacrylate solution, and then the Michael addition reaction was carried out at 60° C. for 24 hours.

Polyethyleneimine suitable for use in the present invention is preferably a linear or branched-type compound having a weight-average molecular weight of 50-10,000 Da. Particularly, it can be a branched-type compound. A solvent that may be used to prepare the polyethyleneimine and glycerol dimethacrylate solutions may be any solvent that can dissolve polyethyleneimine and glycerol dimethacrylate without reacting therewith or decomposing them. Examples of this solvent include dimethylsulfoxide, anhydrous methyl alcohol, ethyl alcohol, dimethylformamide, dioxane, and the like. Preferably, the solvent may be anhydrous methanol.

In step b), the poly(ester amine) formed by the Michael addition reaction is separated. In a preferred example of the present invention, the reaction product was dialyzed against distilled water (dialysis membrane: Spectra/Por, MW cutoff 3.5 k; Spectrum Medical Industries, Inc., LA, Calif., USA) AT 4° C. for 24 hours to separate poly(ester-amine) (PEA). The separated poly(ester amine) can be freeze-dried and stored at 0° C. The freeze drying can be used using a conventional freeze drying method or freeze dryer. As a result, a viscous poly(ester amine) (PEA) from which byproducts were removed can be obtained.

In step c), the separated poly(ester amine) of step b) is reacted with activated vitamin B6 (pyridoxal 5'-phosphate, PLP). Specifically, while the PEA solution was strongly stirred, a solution of pyridoxal 5'-phosphate is added dropwise thereto and reacted at room temperature for 24 hours. As a result, the primary amine of PEA is coupled to pyridoxal 5'-phosphate to form a transient Schiff base. In step d), the reaction product is reduced with NaCNBH$_4$ to convert the primary amine to a secondary amine. As a result, the vitamin B6-coupled poly(ester amine) (VBPEA) gene carrier of formula 1 is obtained. The obtained vitamin B6-coupled poly(ester amine) (VBPEA) gene carrier of the present invention can be purified by any method such as HPLC or dialysis, which is used in the art.

The vitamin B6-coupled poly(ester amine) (VBPEA) gene carrier prepared according to the present invention had a weight-average molecular weight of about 5000-6000 Da as measured by gel permeation chromatography coupled with multiangle laser light scattering (GPC-MALLS). In addition, the content of vitamin B6 in the VBPEA was about 9.77 mol % as analyzed by $^1$H NMR (see FIG. 9). Furthermore, the proton peak of the pyridoxal ring of vitamin B6 in the VBPEA according to the present invention was detected at $\delta$=8.0 ppm, and the proton peak of the PEA backbone was detected at $\delta$=1.1 ppm and 2.4 ppm (see FIG. 9). These results indicate that the vitamin B6-coupled poly(ester amine) (VBPEA) gene carrier according to the present invention was successfully synthesized.

In one aspect, the present invention provides a gene delivery complex composed of a therapeutic gene coupled to the vitamin B6-coupled poly(ester amine) (VBPEA) gene carrier.

The kind of therapeutic gene that may be coupled to the vitamin B6-coupled poly(ester amine) (VBPEA) gene carrier of the present invention is not specifically limited, any gene that can be delivered to a desired target to achieve a desired therapeutic effect falls within the scope of the present invention. For example, genes that can be delivered in combination with the vitamin B6-coupled poly(ester amine) (VBPEA) gene carrier of the present invention include a normal gene comprising a disease-related therapeutic nucleic acid, a gene inhibiting the expression of a target protein, large and small polynucleotides including an antisense polynucleotide, and any RNA-type genes including ribozyme or siRNA. Specifically, the therapeutic gene in the present invention may be selected from the group consisting of siRNAs (small interfering RNAs), siRNAs (small hairpin RNAs), esiRNAs (endoribonuclease-prepared siRNAs), antisense oligonucleotides, DNA, single-stranded RNAs, double-stranded RNAs, DNA-RNA hybrids, and ribozymes. The therapeutic gene in the present invention may be a gene for overexpressing or inhibiting a gene causing a specific disease. Particularly, the therapeutic gene may be a gene corresponding to an siRNA (small interfering RNA), an shRNA (small hairpin RNA), an esiRNA (endoribonuclease-prepared siRNAs) or an antisense oligonucleotide, which inhibits the expression of oncogenes involved in cancer development and progression, or a gene that induces the expression of tumor suppressor genes that are involved in the inhibition of cancer development or progression. Particularly, the therapeutic gene in the present invention may be either a siRNA against serine hydroxymethyltransferase (SHMT) that is a vitamin B6-dependent enzyme playing an important role in the proliferation of cancer cells, or an esiRNA that is a complex mixture thereof. Specifically, the esiRNA may be esiRNA Human SHMT1 (esiRNA1, Sigma, Cat No: EHU159081-50UG).

In an example of the present invention, an esiRNA against SHMT was introduced into cancer cells (A549) by VBPEA, and as a result, it was shown that the VBPEA showed excellent effects on the induction of cancer cell death and the inhibition of cancer cell proliferation compared to other gene carriers (Example 8).

For effective formation of the gene delivery complex according to the present invention, the therapeutic gene and the vitamin B6-coupled poly(ester amine) (VBPEA) are preferably reacted at a molar ratio of 1:0.5 to 1:100, and preferably 1:5 to 1:40.

The present inventors reacted the vitamin B6-coupled poly(ester amine) (VBPEA) with DNA at various molar ratios in order to examine the capability of the VBPEA to condense the therapeutic gene. As a result, it was shown that, when the molar ratio was 1:5 or more, the gene delivery complex (VBPEA/DNA) of the vitamin B6-coupled poly (ester amine) (VBPEA) and DNA was most effectively formed (see A of FIG. 2a), the DNA in the gene delivery complex was effectively protected from DNase cleavage (B of FIG. 2a), and the formed gene delivery complex had a compressed spherical shape (FIG. 2b). In addition, the gene delivery complex according to the present invention showed a relatively uniform particle size distribution of 150-300 nm (FIGS. 2c and 2d), suggesting that it has a particle size suitable for use as a gene carrier. Further, the gene delivery complex showed a positive zeta potential of 30-41 mV (FIG. 2e), suggesting that it can effectively bind to the anionic cell surface.

In order to examine the cytotoxicity of the vitamin B6-coupled poly(ester amine) (VBPEA) of the present invention, the present inventors treated various cells (A549 cells, HeLa cells and HepG2 cells, FIGS. 3a to 3c) with gene delivery complexes, prepared from various molar ratios (5, 10, 20, 30, 40 and 50 N/P) of DNA and VBPEA, under serum-free conditions, and then performed an MTT assay to examine cell viability. The results of the MTT assay were compared to those of the use of PEA and PEI25k. The results of the MTT assay indicated that the VBPEA/DNA complex of the present invention had significantly low cytotoxicity compared to a PEA/DNA complex or a PEI25k/DNA complex (FIGS. 3a to 3c). Specifically, the VBPEA/DNA complex of the present invention showed a cell viability of 98% or higher in A549 cells, HeLa cells and HepG2 cells. In comparison with this, the PEA/DNA complex showed a cell viability of 85-90%, and the PEI25k/DNA complex showed a cell viability of 70%.

In addition, in order to examine the transfection efficiency of the vitamin B6-coupled poly(ester amine) (VBPEA) of the present invention, the present inventors reacted the vitamin B6-coupled poly(ester amine) (VBPEA) with DNA at various molar ratios in various cell lines (A549 cells, HeLa cells, and HepG2 cells; FIGS. 4a to 4c) to form gene delivery complexes (VBPEA/DNA), and then examined the transfection efficiencies of the complexes by a luciferase activity assay (Example 5-1). As a result, it was shown that, when the cells were treated with complexes at various molar ratios of DNA and the vitamin B6-coupled poly(ester amine) (VBPEA), the complexes showed similar transfection efficiencies at a molar ratio of 1:10 to 1:40. Particularly, a PEI 25K-treated group used as a control group showed a rapid decrease in gene delivery efficiency as the molar ratio increased, whereas the gene delivery complexes of the present invention maintained high transfection efficiency regardless of the molar ratio and stably maintained high transfection efficiency even in the presence of serum, compared to the PEI 25K-treated group that showed a rapid decrease in transfection efficiency (see FIG. 4d).

In addition, in order to examine the in vitro transfection efficiency of the vitamin B6-coupled poly(ester amine) (VBPEA) of the present invention, the present inventors analyzed the GFP expression of VBPEA in A549 cells by flow cytometry (Example 5-2). As a result, it was shown that the PEA/DNA complex showed a transfection efficiency of 30-35% and the PEI25k/DNA complex had a transfection efficiency of 10-13%, whereas the VBPEA/DNA complex had a transfection efficiency of 40-45% (FIGS. 4e and 5).

Also, in order to examine the biodistribution and transfection efficiency of the vitamin B6-coupled poly(ester amine) (VBPEA) of the present invention, the present inventors administered a VBPEA/pGL3 complex to Balb/c mice (four animals per group) by intravenous injection and analyzed the biodistribution thereof. As a result, it was shown that luciferase activity was higher in the order of the spleen, the lungs, the brain, the liver, the kidneys and the heart (FIG. 4f).

The above-described results suggest that the vitamin B6-coupled poly(ester amine) (VBPEA) of the present invention effectively a nano-sized gene delivery complex due to its excellent ability to bind to DNA, and thus high transfection efficiency that is stably maintained even in the presence of serum, indicating that it can be advantageously used in vivo. This high transfection efficiency of the vitamin B6-coupled poly(ester amine) (VBPEA) of the present invention is attributable to the buffering capacity of the copolymer.

In order to demonstrate the mechanism of high transfection efficiency of the vitamin B6-coupled poly(ester amine) (VBPEA) as described above, the present inventors performed experiments.

To examine the role of vitamin B6 in the transfection of the VBPEA of the present invention, a competitive inhibition experiment was performed using 4'-deoxypyridoxine that is a structural analogue of vitamin B6. As a result, it was shown that when treatment with 4'-deoxypyridoxine (1 mM) was performed, the transfection efficiency of the VBPEA/

DNA complex was rapidly reduced compared to that of the PEA/DNA complex. This suggests that the high transfection efficiency of the VBPEA/DNA complex is because vitamin B6 binds to VTC (VB6 transporting membrane carrier) (FIG. 6A).

In addition, to examine the intracellular uptake pathway of the VBPEA/DNA complex, various endocytosis pathways were inhibited, and then the comparison of transfection efficiency was performed. Clathrin-mediated endocytosis was inhibited using its inhibitor chlorpromazine, and caveolae-mediated uptake was inhibited using its inhibitor β-methyl cyclodextrin or genistein. As a result, it was found that when treatment with the caveolae inhibitors β-methyl cyclodextrin or genistein was performed, the VBPEA-mediated or PEA-mediated transfection efficiency decreased in a concentration-dependent manner. This suggests that the two gene carriers use the caveolar uptake pathway.

Further, in order to examine the proton sponge effect of PEI constituting the VBPEA, treatment with bafilomycin A1 (vacuolar type $H^+$ ATPase specific inhibitor, 200 nM) that is an endosome proton pump inhibitor was performed, and then the comparison of transfection efficiency was performed. When the vacuolar-type proton pump was inhibited using bafilomycin A1 as described above, the transfection of VBPEA decreased by about 1000 times. This suggests that the transfection of VBPEA is promoted by the proton sponge effect (FIG. 12).

Thus, it can be seen that the vitamin B6-coupled poly (ester amine) (VBPEA) of the present invention shows a high ability to bind to DNA, effectively protects DNA from DNase, and can form a spherical gene delivery complex having a uniform particle size, which is suitable for use as a gene carrier. In addition, it can adhere to the cell membrane through vitamin B6 receptor, and thus can be easily taken up by cells. Also, it has an increased duration time in the cytoplasm, exhibits physiochemical properties suitable for use as a gene carrier, shows a very low cytotoxicity in vitro and in vivo, and shows a very high transfection efficiency. Thus, it can be effectively used as a gene carrier for gene therapy.

In one aspect, the present invention a pharmaceutical formulation for gene therapy, which comprises, as active ingredient, a gene delivery complex composed of a therapeutic gene coupled to the vitamin B6-coupled poly(ester amine) (VBPEA) gene carrier. The pharmaceutical formulation of the present invention can be used for the treatment or prevention of various diseases depending on the kind of therapeutic gene.

The pharmaceutical formulation of the present invention may be administered together with a pharmaceutically acceptable carrier. For oral administration, the pharmaceutical formulation may comprise, in addition to the active ingredient, a binder, a lubricant, a disintegrant, an excipient, a solubilizer, a dispersing agent, a suspending agent, a pigment, a fragrance, and the like. For administration by injection, the pharmaceutical formulation of the present invention may comprise a buffer, a preservative, a pain-relieving agent, a solubilizing agent, an isotonic agent, a stabilizer and the like. For topical administration, the formulation of the present invention may comprise a base, an excipient, a lubricant, a preservative and the like.

The formulation of the present invention can be formulated into various forms using the pharmaceutically acceptable carriers as described above, and particularly, can be prepared as formulations for inhalation or injection. For example, for oral administration, the formulation can be formulated in the form of tablets, troches, capsules, elixirs, suspensions, syrups, wafers or the like, and for administration by injection, it can be formulated in the form of unit dosage ampoule or multiple dosage container. In addition, it may be formulated in the form of solutions, suspensions, tablets, pills, sustained-release preparations or the like. Drug delivery through inhalation is a non-invasive method, and delivery of therapeutic genes through formulations (e.g., aerosol) for inhalation can be advantageously used for treatment of lung disease. This because the anatomical structure and location of the ling make a simple, non-invasive approach possible and can receive topical application of the gene delivery system without affecting other organs.

Examples of the carrier, excipient and diluent suitable for formulation include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulation of the present invention may further include fillers, anti-coagulating agents, lubricants, wetting agents, flavors, preservatives and the like.

The pharmaceutical formulation of the present invention can be administered orally or parenterally. Specifically, the pharmaceutical formulation of the present invention can be administered orally, intravenously, intramuscularly, intrarterially, intramedullarly, intradurally, intracardially, intraperitoneally, transdermally, subcutaneously, enterally, sublingually or topically, but is not limited thereto. For such clinical administration, the pharmaceutical formulation of the present invention can be formulated into suitable forms using a known technique. For example, for oral administration, the pharmaceutical formulation can be mixed with an inactive diluent or an edible carrier, be filled in hard or soft gelatin capsules or be pressed into tablets. In case of oral administration, the active compound is mixed with an excipient and is used in form of tablets for intake, buccal tablets, troches, capsules, elixir, suspension, syrup, wafers and the like. For injection or parenteral administration, various formulations can be prepared using conventional techniques known in the art.

The effective dosage of the pharmaceutical formulation of the present invention varies depending on the patient's body weight, age, sex, health conditions, diet, the period of administration, the mode of administration, excretion rate, the severity of the disease, etc., and can easily determined by one of ordinary skill in the art.

The therapeutic agent in the pharmaceutical formulation of the present invention may be one that inhibits the expression of serine hydroxymethyltransferase (SHMT). Specifically, it may be esiRNA Human SHMT1 (esiRNA1, Cat No: EHU159081-50UG). The pharmaceutical formulation of the present invention can be used for the prevention or treatment of cancer depending to the kind of therapeutic gene, and the cancer can be selected from the group consisting of lung cancer, bone cancer, pancreatic cancer, skin cancer, head and neck carcinoma, melanoma, uterine cancer, ovarian cancer, rectal cancer, colorectal cancer, colon cancer, breast cancer, uterine sarcoma, fallopian tube carcinoma, endometrial cancer, cervical cancer, vaginal carcinoma, vulva cancer, esophageal cancer, small intestine cancer, thyroid cancer, parathyroid cancer, soft tissue sarcoma, urethral cancer, penis cancer, prostate cancer, chronic or acute leukemia, pediatric solid tumors, differentiated lymphoma, bladder cancer, renal cancer, renal cell carcinoma, renal pelvic carcinoma, primary central nervous system lymphoma, spinal cord tumor, brain stem glioma, and pituitary adenoma.

In still another aspect, the present invention provides a gene therapy method employing the above-described VBPEA gene carrier, a gene delivery complex comprising the same, or a pharmaceutical formulation comprising the same.

Advantageous Effects

The vitamin B6-copuled poly(ester amine) (VBPEA) gene carrier according to the present invention, when used as a complex with DNA, has a significantly high gene delivery rate, little or no cytotoxicity, and a very high in vivo transfection efficiency. In addition, a complex of VBPEA with siRNA shows high gene silencing efficiency and has high abilities to induce cancer cell death and inhibit cancer cell proliferation, and thus it can be used for anticancer therapy. Accordingly, the gene carrier VBPEA of the present invention can be used as an experimental gene carrier and can also be widely used in gene therapy against various diseases depending on the kind of therapeutic gene.

DESCRIPTION OF DRAWINGS

FIG. 3a shows the results for A549 cells, 3b shows the results for HeLa cells, and FIG. 3c shows the results for HepG2 cells.

FIG. 4a shows the results for A549 cells, FIG. 4b shows the results for HeLa cells, and FIG. 4c shows the results for HepG2 cells.

FIG. 7A-C shows the results of experiments conducted to analyze the transfection mechanism of the vitamin B6-coupled poly(ester amine) (VBPEA). Specifically, FIG. 7A shows the results of analyzing the influence of treatment with vitamin B6 and treatment with the VBPEA gene carrier on the promotion of transfection. FIG. 7B shows a comparison of the transfection efficiency of a VBPEA/DNA complex in human or mouse lung cells or lung cancer cells. FIG. 7C shows the results of an experiment conducted to examine whether the use of the VBPEA gene carrier makes gene silencing possible.

MODE FOR INVENTION

Figure 1:
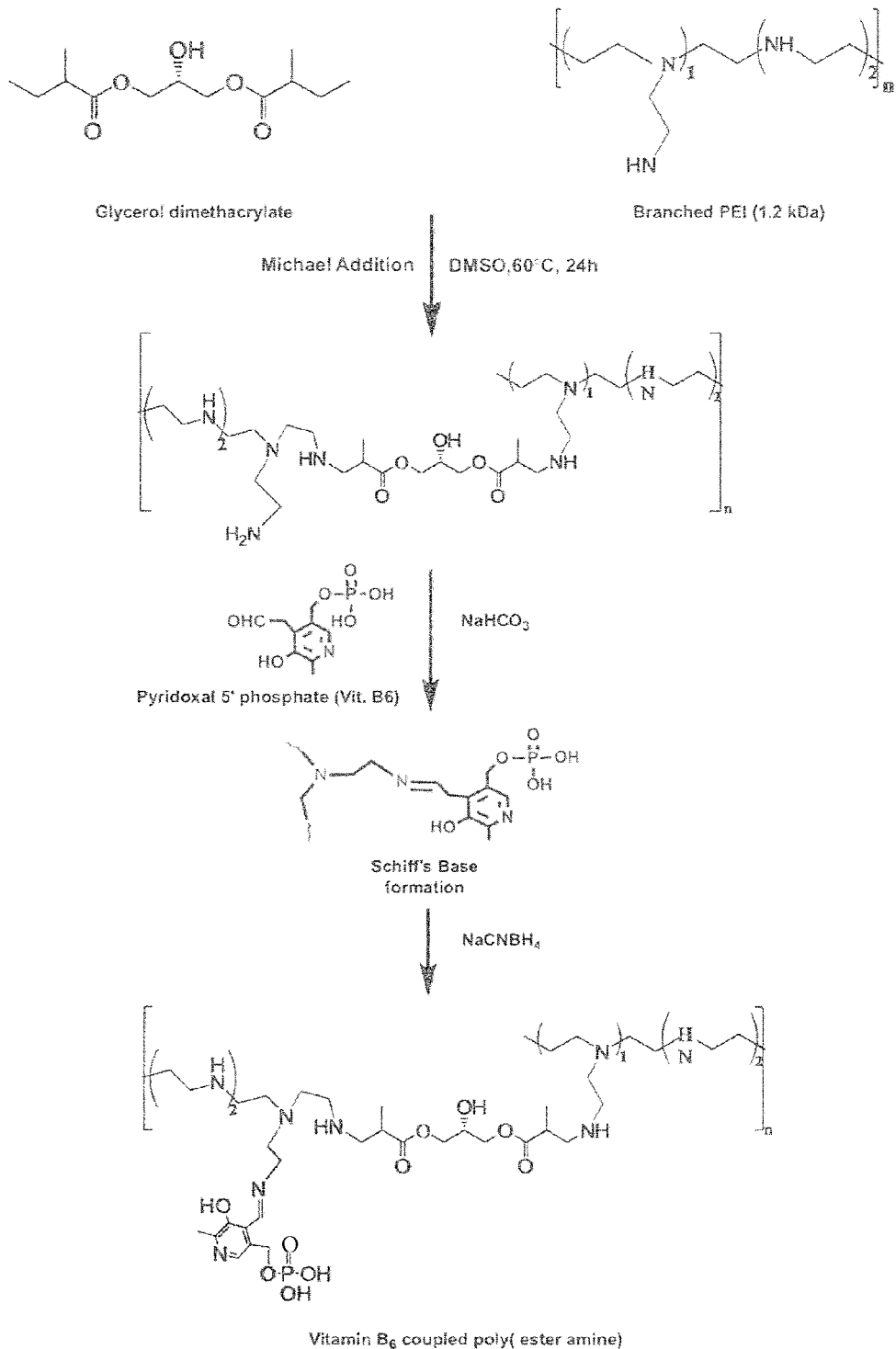
FIG. 1 shows a process for synthesizing a vitamin B6-coupled poly(ester amine) (VBPEA) gene carrier according to the present invention.

Hereinafter, the present invention will be described in further detail with reference to examples. It is to be understood, however, that these examples are for illustrative purposes only and are not intended to limit the scope of the present invention.

Examples 1: Reagents and Materials Used

In the present invention, the vitamin B6-coupled poly (ester amine) (VBPEA) gene carrier of the present invention was prepared, and the following materials and reagents were used in the following examples and experimental examples: bPEI (branched poly(ester imine), Mn: 1.2 k and 25 k), DMSO (dimethyl sulfoxide), PLP (pyridoxal 5'-phosphate), NaCNBH$_4$ (sodium cyanoborohydride), genistein, Chlorpromazine, methyl-β-cyclodextrin, bafilomycin A1, MTT (3-(4,5-dimethyl thioazol-2-yl)-2,5-diphenyl tetra-zolium bromide) reagent and 4'-4'-deoxylpyridoxine hydrochloride were obtained from Sigma (St. Louis, Mo., USA). Moreover, a firefly (*Photonus pyralis*) luciferase-encoding luciferase reporter, a pGL3-vectoor and an enhancer were obtained from Promega (Madison, Wis., USA). GFP (green fluorescent protein) gene was obtained from Clontech (Palo Alto, Calif., USA). Confocal microscopic analysis was performed using TRITC (tetramethylrhodamine isothiocyanate) and YOYO-1 iodide (Molecular Probes, Invitrogen, Oregon, USA) dyes. Nonspecific scrambled siRNA (siScr) and luciferase siRNA shown in Table 1 below were purchased from Genolution Pharmaceuticals, Inc. (Seoul, Korea). All the compounds in the following examples and experimental examples were of analytical reagent grade.

In brief, the VBPEA gene carrier was prepared by a two-step reaction comprising cross-linking low-molecular-weight bPEI with glycerol dimethacrylate (GDM) to prepare PEA (poly(ester amine), and coupling B6 (pyridoxal 5'-phosphate (PLP) to the prepared PEA (poly(ester amine). The detailed process is as follows.

2-1: Step of Preparing PEA

PEA was prepared by the Michael addition reaction between low-molecular-weight bPEI (1.2 k) and GDM. Specifically, each of GDM and low-molecular-weight bPEI was dissolved in anhydrous methanol, the low-molecular-weight bPEI solution was slowly added to the GDM solution at 60° C. and a constant stirring rate for 24 hours such that the stoichiometric ratio was 1:2. The reaction mixture was dialyzed in distilled water 4° C. for 24 hours using a Spectra/Por membrane (MW cutoff 3.5 k; Spectrum Medical Industries, Inc., LA, Calif., USA). The resulting material was freeze-dried and stored at 0° C.

2-2: Step of Preparing VBPEA

In the presence of the PEA prepared in Example 2-1, 10 mol % of primary amine was reacted with pyridoxal 5'-phosphate (PLP) to form a transient Schiff base. Then, the Schiff base was reduced with NaCNBH$_4$ to obtain VBPEA. Specifically, 10 mL of PLP solution (25 mg/mL) was added dropwise to 50 mL of an aqueous solution containing 1 g of PEA and 100 mg of NaHCO$_3$. The dropwise addition was performed with strong stirring at room temperature for 24 hours.

Then, in order to reduce the produced Schiff base into secondary amine, 50 mg of NaCNBH$_4$ was added thereto. The reaction mixture was dialyzed in distilled water 4° C. for 24 hours using a Spectra/Por membrane (MW cutoff 3.5 k; Spectrum Medical Industries, Inc., LA, Calif., USA). The resulting material was freeze-dried and stored at 0° C.

As a result, the terminal amine of PEA reacted with the aldehyde group of vitamin B6 (pyridoxal 5'-phosphate) to form an unstable transient Schiff base which was then reduced with NaCNBH$_4$. For the produced VBPEA, the structure, the abilities to condense and protect DNA, the size, the zeta potential and the DNA complex shape were analyzed.

TABLE 1

| siRNA sequence | | |
|---|---|---|
| siRNA | Sense (5'->3') | Antisense (5'->3') |
| siRNA scrambled (siScr) | CGUACGCGGAAUACUUCGAUU (SEQ ID NO: 1) | UCGAAGUAUUCCGCGUACGUU (SEQ ID NO: 2) |
| siRNA Luciferase (siLuc) | CUUACGCUGAGUACUUCGAUU (SEQ ID NO: 3) | UCGAAGUACUCAGCGUAAGUU (SEQ ID NO: 4) |
| siRNA Serine hydroxymethyltransferase (siSHMT) | esiRNA Human SHMT1 (esiRNA1, Cat No: EHU159081-50UG) (Complex mixture having no specified sequence) | |

Example 2: Preparation of Vitamin B6-Coupled Poly(Ester Amine) Gene Carrier

The vitamin B6-coupled poly(ester amine) (VBPEA) gene carrier according to the present invention was synthesized according to the Michael addition reaction that is a slight modification of the method described in Arote R B, et al., Bioconjug. Chem. 2009, 20(12): 2231-41) (FIG. 1).

2-3. Analysis of Properties of Vitamin B6-Coupled Poly (Ester Amine)

The structures of the freeze-dried vitamin B6-coupled poly(ester amine) (VBPEA) and PEA were analyzed by $^1$H-nuclear magnetic resonance ($^1$H-NMR) (Advanced 600, Bruker, Germany, 600 mHz). The absolute molecular weight of VBPEA was measured by gel permeation chromatography coupled with multiangle laser light scattering (GPC-MALLS) using Sodex OHpack SB-803 HQ (Phenomenex, Torrells, Calif., USA). The chromatography analysis was performed at a flow rate of 0.5 ml/min and a temperature of 25° C.

Figure 9:
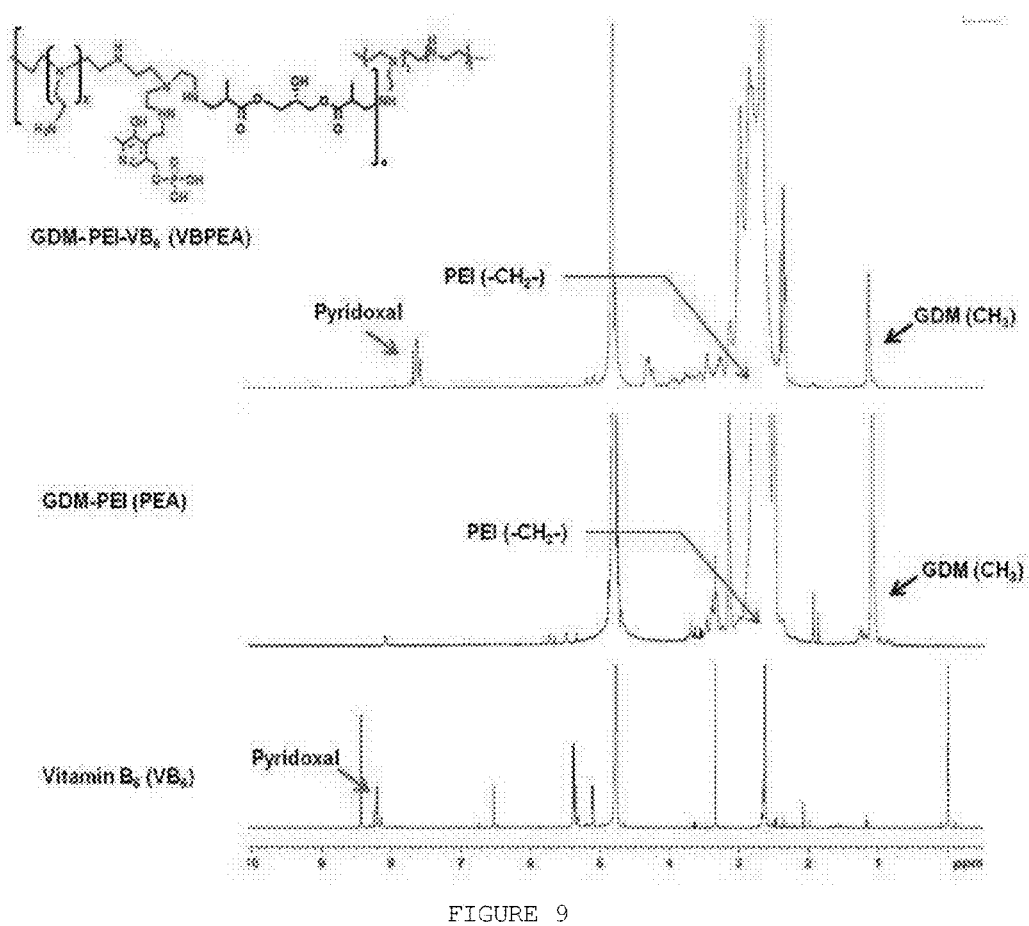
FIG. 9 is a graph showing the results of analyzing the structure of a freeze-dried vitamin B6-coupled poly(ester amine) (VBPEA) by $^1$H-nuclear magnetic resonance ($^1$H-NMR; Avance 600, Bruker, Germany, 600 mHz).
Figure 10:
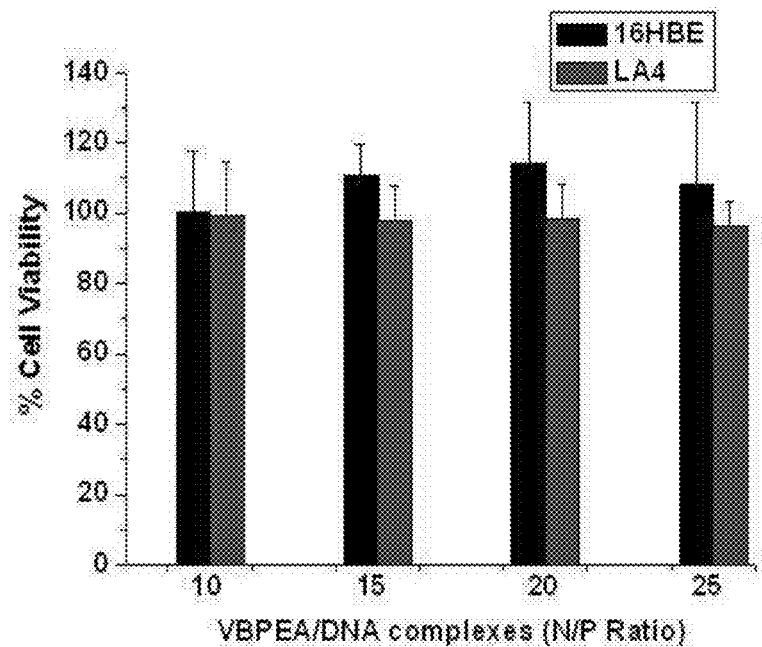
FIG. 10 shows the results of analyzing the cytotoxicity of the inventive vitamin B6-coupled poly(ester amine) (VBPEA) against human and mouse normal lung cells (16HBE-human, LA4-mouse) (n=3, error bar=SD).

When the structure of VBPEA was analyzed by $^1$H-nuclear magnetic resonance, a strong peak appeared at 8.0 ppm, indicating a proton present on the pyridoxal ring of vitamin B6. The PEA backbone was confirmed by methyl peaks at 1.1 ppm and 2.4 ppm. The comparison of the NMR data of vitamin B6, PEA and VBPEA can be seen in FIG. 9. The content of vitamin B6 in VBPEA was about 9.77 mol % as determined by the NMR analysis (FIG. 10).

In addition, the molecular weight of VBPEA was about 5000-6000 Da as measured by the GPC-MALLS. The above results are summarized in Table 2 below.

TABLE 2

Structural properties of VBPEA

| Sample | Molecular weight (Da) of reactants PEA | VB$_6$ | PEA (mol-%) | VB$_6$ (mol-%) | Molecular weight (Da) | Poly-dispersity index (PDI) |
|---|---|---|---|---|---|---|
| VBPEA | 5000-5200 | 247 | 90.23 | 9.77 | 5000-6150 | 1.12 |

Example 3: Analysis of Properties of Vitamin B6-Coupled Poly(Ester Amine)/DNA Complex 3-1. DNA Condensation Capability of VBPEA One of the most properties of gene carriers is the capability to condense plasmid DNA by interaction therewith. Accordingly, the DNA condensation capability of the vitamin B6-coupled poly(ester amine) (VBPEA) prepared in Example 2 was analyzed by a gel retardation assay.

Specifically, VBPEA was mixed with a pGL3 plasmid (5.3 kb, Promega) at various molar ratios (N/P ratios) of 0.5, 1, 3, 5 and 10, and the mixture was adjusted with a total volume of 20 ul with autoclaved water. Each of the solutions was lightly vortexed and incubated at room temperature for 30 minutes, and 1× loading dye (Biosesang, Korea) was added thereto. Then, each of the reaction solutions was electrophoresed (100 V) on 0.8% agarose gel, and the mobility of DNA was observed under UV light. As a control, the pGL3 plasmid alone was used without reacting with VBPEA.

Figure 2A:
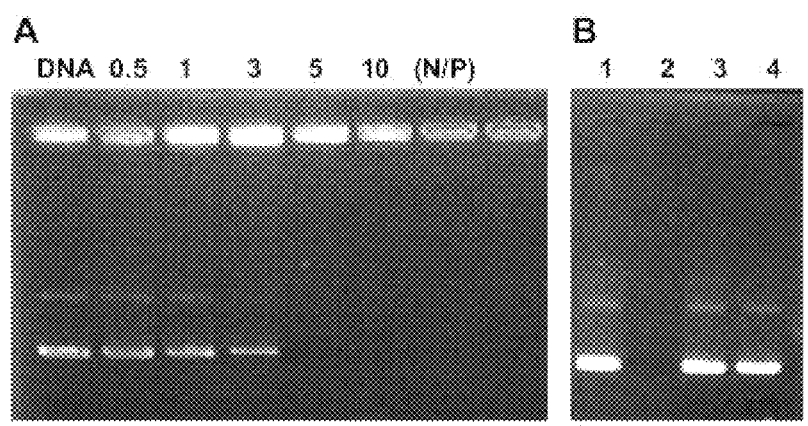
FIG. 2a shows the results of reacting the vitamin B6-coupled poly(ester amine) (VBPEA) with DNA at various molar ratios in order to examine the capability of the vitamin B6-coupled poly(ester amine) (VBPEA) to condense a therapeutic gene.

As a result, as can be seen in FIG. 2a, when the N/P ratio was 5, the migration of gel was completely retarded. This suggests that the VBPEA of the present invention had a high ability to bind to DNA and effectively condensed the plasmid DNA to form a gene delivery complex (VBPEA/DNA). Unreacted plasmid DNA as a control migrated through the gel without retardation. As can be seen from the above results, it is preferred to mix plasmid DNA with the VBPEA of the present invention at a N/P ratio of 5 or higher for effective formation of a gene delivery complex.

3-2. DNA Protecting Effect of VBPEA

For effective gene expression, DNA in a gene delivery complex should be protected from enzymes such as DNase. To examine this DNA protecting effect, the vitamin B6-coupled poly(ester amine) (VBPEA) prepared in Example 2 and pGL3 plasmid DNA were mixed with each other at a molar ratio (N/P ratio) of 10:1 and reacted at room temperature for 30 minutes to prepare a gene delivery complex (VBPEA/DNA). To DNase/Mg$^2$ lysis buffer (50 mM Tris Cl, pH 7.6, and 10 mM MgCl$_2$) containing 4 μl of the gene delivery complex solution or unreacted plasmid DNA, 1 μl (50 units) of DNase I was added and the mixture was incubated with stirring at 37° C. for 30 minutes. Next, the reaction solution was treated with 4 μl of EDTA (250 mM, 1N NaOH) at room temperature for 30 minutes to stop the enzymatic reaction, and then 5 μl of 1% sodium dodecyl sulfate (pH 7.2) was added to the solution which was then incubated at 25° C. for 2 hours in order to break the ionic bond between VBPEA and DNA. After incubation, the solution containing the separated DNA was electrophoresed on 0.8% agarose gel at 100 V for 40 minutes using tris-acetate-EDTA buffer (1×TAE running buffer).

Figure 2B:
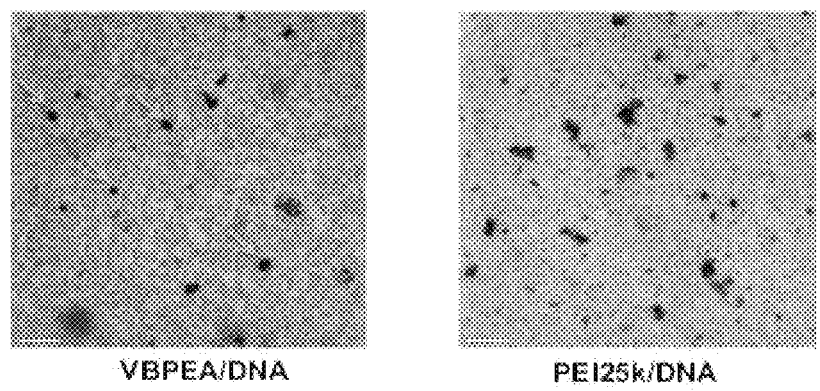
FIG. 2b shows the results of agarose gel electrophoresis conducted to examine whether a gene delivery complex obtained by reacting the vitamin B6-coupled poly(ester amine) (VBPEA) of the present invention with a therapeutic gene protects DNA when it is treated with DNAseI.

As a result, as can be seen in FIG. 2b, the untreated plasmid DNA as the control was completely degraded by DNase I (lane 2), whereas the DNA in the gene delivery complex (VBPEA/DNA) of the present invention was effectively protected from degradation by DNase I (lane 4). Such results indicate that the gene delivery complex of the present invention can effectively deliver DNA into cells while protecting DNA from the attack of DNase.

3-3. Morphological Analysis of VBPEA Gene Carrier/DNA Complex

The morphology of the gene delivery complex (VBPEA/DNA), prepared in Example 3-1 by reacting the vitamin B6-coupled poly(ester amine) with pGL3 plasmid DNA at a molar ratio N/P ratio) of 20:1, was observed with a transmission electron microscope (LIBRA 120, Carl Zeiss, Germany). Specifically, a VBPEA/DNA complex (N/P: 20) and a PEI25k/DNA complex (N/P: 10) as a control were prepared, loaded onto a carbon grid and stained with 1% uranyl acetate for 10 seconds, followed by washing with distilled water. Next, the samples were dried for 10 minutes, and then observed with an electron microscope.

Figure 2C:
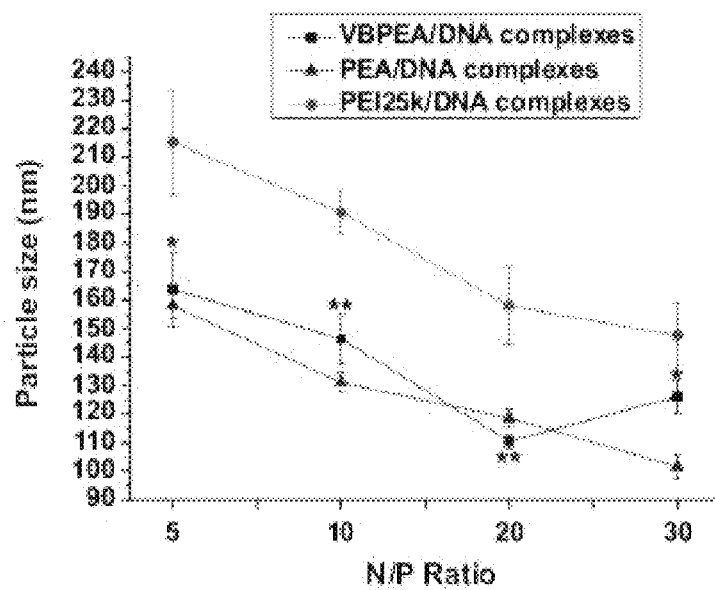
FIGS. 2c and 2d show the results of measuring the particle size of the inventive gene delivery complexes prepared at various N/P ratios (5, 10, 20 and 30) under serum-free conditions (FIG. 2c) and the particle size of the inventive gene delivery complexes prepared in the presence of various concentrations (0%, 10%, 20% and 30%) of serum (FIG. 2d).
Figure 2D:
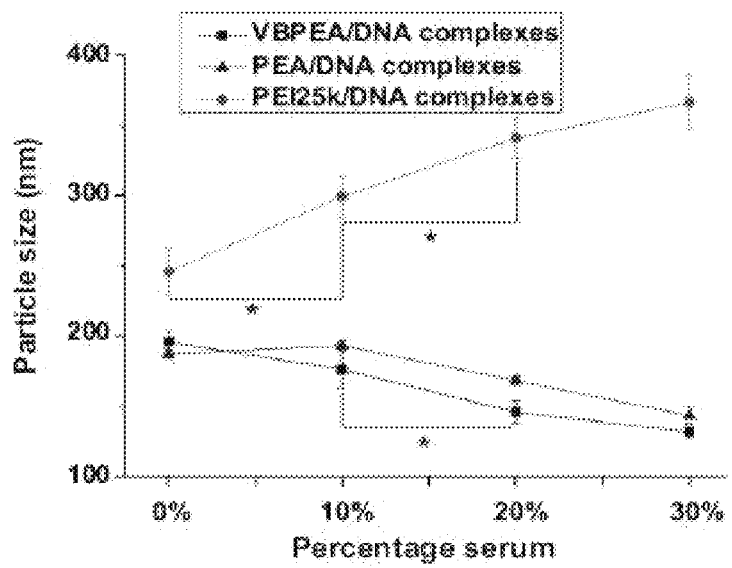
Figure 2E:
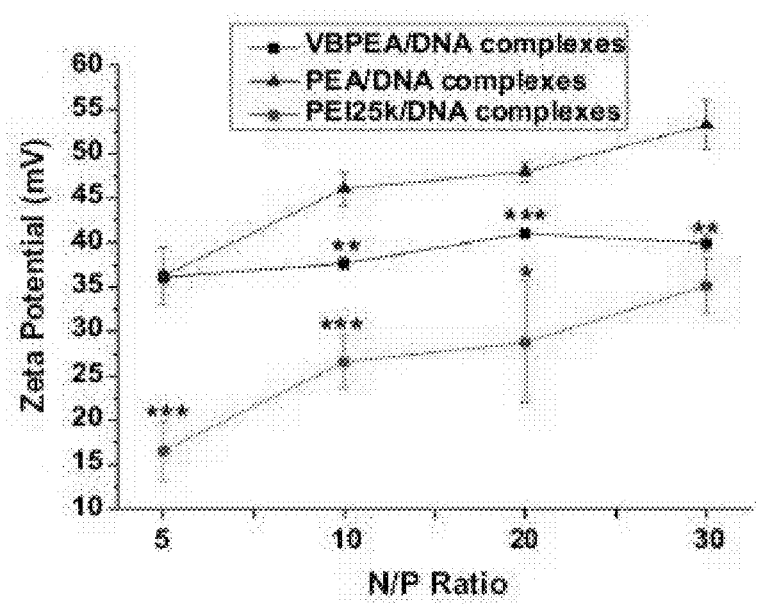
FIG. 2e shows the results of measuring the zeta potential of the inventive gene delivery complexes prepared at various N/P ratios (5, 10, 20 and 30).

As a result, as can be seen in FIG. 2d, the VBPEA/DNA complex of the present invention had a nano-scale particle size suitable for cell uptake.

3-4. Measurement of Surface Charge of VBPEA Gene Carrier/DNA Complex

The positive surface charge of the gene delivery complex is essential for binding to the anionic cell surface and facilitates the intracellular internalization of the complex. Accordingly, the zeta potentials of gene delivery complexes (VBPEA/DNA), formed by reacting the vitamin B6-coupled poly(ester amine) of the present invention with plasmid DNA at various molar ratios, and a PEA/DNA complex and a PEI25k/DNA complex as controls, were measured using a dynamic light scattering spectrometer (DLS-8000, Otsuka Electronics, Osaka, Japan) at 25° C. and at scattering angles of 90° and 20°. Each of the samples was incubated at N/P ratios of 5, 10, 20 and 30 in such a manner that the final concentration of DNA in a total volume of 1 mL was 40 μg/mL. In order to examine the influence of serum protein on the stability of the VBPEA/DNA complex (N/P: 20) compared to those of the PEA/DNA complex (N/P: 20) and the PEI25k/DNA complex (N/P: 10), the particles sizes of the gene delivery complexes were measured in the presence of various concentrations (0%, 10%, 20% and 30%) of serum.

The results of observation with the dynamic light scattering spectrometer (DLS) indicated that the size of the VBPEA/DNA complex decreased as the N/P ratio or the concentration of serum increased. However, it was shown that the VBPEA/DNA complex of the present invention showed an increase in zeta potential from 35 mV to 41 mV with an increase in the N/P ratio, even though this increase was insignificant compared to that of the PEA/DNA or PEI25k/DNA complex (FIG. 2f). The gene delivery complex prepared by the VBPEA of the present invention with plasmid DNA at a molar ratio of 20:1 showed the highest positive zeta potential. This positive surface charge indicates that the positively charged DNA is completely encapsulate in the gene delivery complex. Also, this positive surface charge has advantages in that it facilitates the intracellular internalization of the gene delivery complex and causes an electrostatic repulsive force between the complex particles to reduce the aggregation of the particles.

After a specific aggregation limit (~110 nm; N/P: 20) was reached, the particle size started to increase again, probably because of the electrostatic repulsive force in the complex. Meanwhile, the insignificant increase in zeta potential compared to that of the PEA/DNA complex is believed to be because of coupling with vitamin B6. In addition, the continuous increase in size of the PEI25k/DNA complex by aggregation with serum protein according to the increase in the concentration of serum suggests that the PEI25k/DNA complex is not suitable for cell uptake. However, it was shown that there was little or no change in the size of the VBPEA/DNA complex according to the concentration of serum. This is believed to be because the coupling between the hydroxyl group of the PEA backbone and vitamin B6 interferes with the binding between the positive charge of the PEA backbone and serum protein.

In addition, EF-TEM images showed that the VBPEA/DNA complex had a uniform particle size distribution (120 nm or less) (FIG. 2c). Particularly, it was shown that the VBPEA/DNA complex had a spherical shape readily distinguishable from that of the PEI25k/DNA complex and did not aggregate, suggesting that it can be easily internalized into cells.

Example 4: Analysis of In Vitro Transfection Efficiency of Vitamin B6-coupled poly(ester amine)

4-1. Isolation and Culture of Mouse Primary Lung Cells

A human lung adenocarcinoma cell line (A549) and a mouse lung epithelial cell line (LA-4) were cultured in RPMI-1640 medium. A human cervical cancer cell line (HeLa) and a human hepatoma cell line (HepG2) were cultured in DMEM (low glucose) medium. A human bronchial epithelial cell line (16HBE) was cultured in DMEM/Ham's F12 medium (FBS, HyClone, Logan, Utah, USA) containing 10% heat-inactivated fetal bovine serum and 1% penicillin/streptomycin. All the cells were cultured in a standard culture environment at 37 t under 5% $CO_2$.

To obtain a lung single cell suspension, lungs were extracted from mice (6 weeks old) and stored in DMEM/F-12 medium containing 0.5 mg/mL collagenase D (Roche Applied Science, Indianapolis, Ind., USA) and 100 µg/mL of DNase I (Sigma-Aldrich). The tissue was cut with scissors, incubated at 37° C. for 1 hours, and then passed through a 70 µm Falcon cell strainer (BD Labware). RBC lysis was performed by centrifugation (800 rpm, 10 min) using ACK lysis buffer (Gibco). The cell pellets were resuspended in DMEM/Ham's F-12 medium (containing 10% FBS and 1% antibiotic), and the cells were counted and seeded in a 24-well plate.

4-2. Cytotoxicity of Vitamin B6-Coupled Poly(Ester Amine)

To examine the cytotoxicity of the vitamin B6-coupled poly(ester amine) (VBPEA), various cells were treated with gene delivery complexes, prepared from various molar ratios (5, 10, 20, 30, 40 and 50 N/P) of DNA and VBPEA under serum-free conditions, and the cell viability was analyzed by an MTT assay. The cell viability was compared with those of cells treated with PEA and PEI25k.

Specifically, before treatment with the complexes, each of A549 cells, HeLa cells and HepG2 cells was seeded into each well of a 24-well plate at $1\times10^5$ cells/mL and cultured to a confluence of 80% in a 5% $CO_2$ incubator at 37° C. The vitamin B6-coupled poly(ester amine) of the present invention or PEI and DNA were mixed at various N/P ratios to prepare gene delivery complexes, and the medium of the cells cultured as described above was replaced with serum-free medium, followed by incubation for 3 hours. Then, the medium was replaced with serum-containing medium. After incubation for 36 hours, each well was treated with 500 µl of MTT reagent (0.5 mg/mL in 1×PBS) and incubated for 3 hours. After removing medium, formazan in each well was dissolved with DMSO, and the colored solution was transferred to a 96-well plate, and the optical density at 540 nm was measured with VERSAmax tunable microplate reader (Sunnyvale, USA). All the experiments were repeated three times.

Figure 3A:
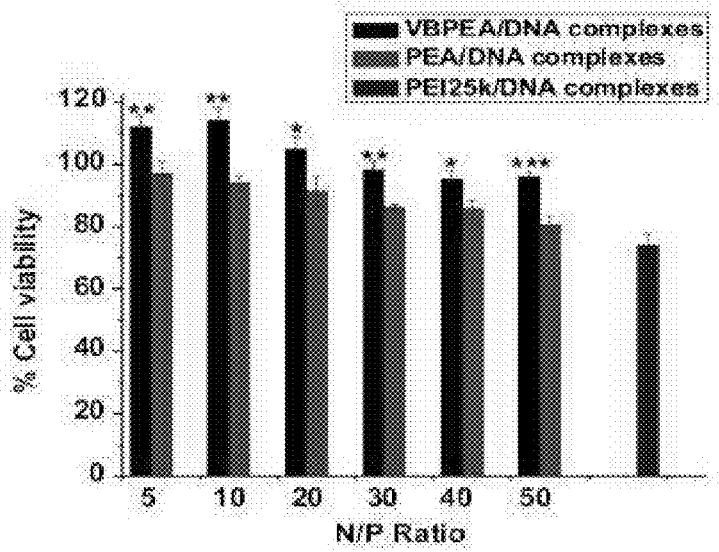
FIGS. 3a to 3c show the cell viability of various cells treated with gene delivery complexes prepared at various N/P ratios (5, 10, 20, 30, 40 and 50 N/P) under serum-free conditions. Specifically.
Figure 3B:
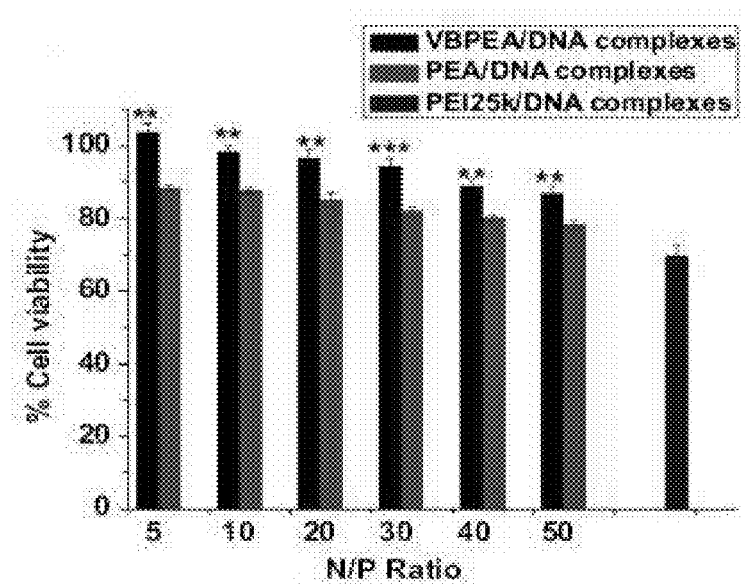
Figure 3C:
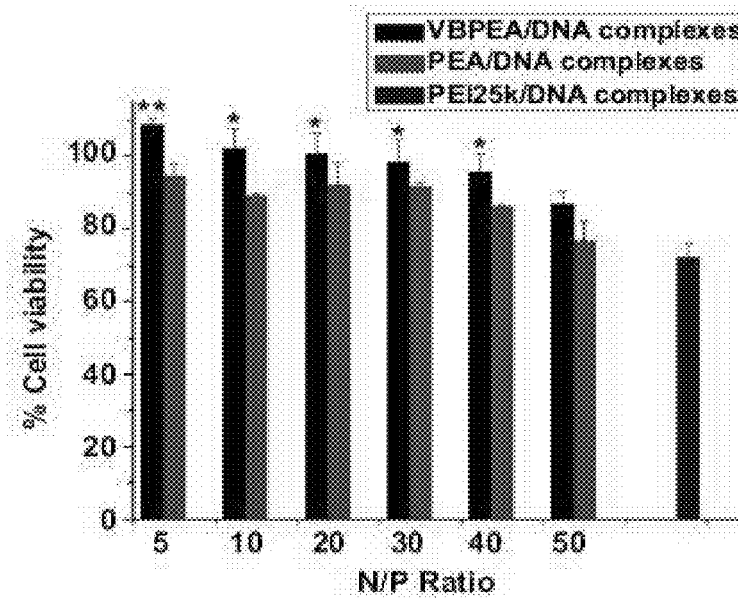

The results of the MTT assay indicated that the cytotoxicity of the VBPEA/DNA complex of the present invention was significantly lower than that of the PEA/DNA or PEI25k/DNA complex (FIG. 3). Specifically, the VBPEA/DNA complex of the present invention showed a cell viability of 98% or higher in A549 cells, HeLa cells and HepG2 cells. However, the PEA/DNA complex showed a cell viability of 85-90%, and the PEI25k/DNA complex showed a cell viability of 70%.

Example 5: Analysis of In Vitro and In Vivo Transfection Efficiencies of Vitamin B6-Coupled Poly(Ester Amine)

5-1. Analysis of In Vitro Transfection by Luciferase Assay

In order to examine the transfection efficiency of the vitamin B6-coupled poly(ester amine) (VBPEA) of the present invention in the presence or absence of serum, a transfection experiment was performed in various cell lines.

Specifically, each of the A549 cell line, the HeLa cell line and the HepG2 cell line was seeded into each well of a 24-well plate at a density of $1\times10^5$ cells/well. The cells were grown to a confluence of 80%, and then treated with VBPEA/pGL3 plasmid, PEA/pGL3 plasmid or PEI25k/pGL3 plasmid complexes, prepared at various molar ratios (5, 10, 20, 30, 40 and 50 N/P) under serum-free conditions. After 3 hours, the medium was replaced, and the cells were incubated for 24 hours under standard incubation conditions. Then, the cells were subjected to a luciferase assay according to the manufacturer's protocol. Relative light units (RLU) were measured using a chemiluminometer (Autolumat, LB953; EG&G Berthold, Germany) and normalized to protein concentrations using a BCA protein assay kit (Perice Biotechnology, Rockford, Ill., USA).

Meanwhile, in order to examine the influence of serum on the stability of the complexes, the A549 cell line in a 24-well culture dish was transfected with each of complexes (prepared at a N/P ratio of 20) at various serum concentrations of 0, 10, 20 and 30%. Then, a luciferase assay was performed in the same manner as described above. The transfection efficiency was measured as RLU/mg (protein), and the experiment was repeated three times.

As a result, as can be seen in FIG. 4, the transfection efficiency (luciferase expression) of the VBPEA/DNA complex of the present invention was 5-20 times higher than that of the PEA/DNA complex and 12-30 times higher than that of the PEI25k/DNA complex.

5-2. Analysis of In Vitro Transfection by Flow Cytometry

In order to examine the in vitro transfection efficiency of the vitamin B6-coupled poly(ester amine) (VBPEA) of the present invention, the GFP expression of VBPEA in A549 cells was analyzed by flow cytometry.

Specifically, the VBPEA of the present invention and the plasmid pcDNA3.1/CT-GFP (6.1 kb, Invitrogen) expressing green fluorescent protein (GFP) were mixed with each other at a molar ratio of 10 to prepare a gene delivery complex (VBPEA/tGFP). A549 cells were transfected with the prepared VBPEA/tGFP complex, after which the cells washed with PBS and treated with trypsin. 10,000 cells were analyzed using FACS Calibur System (Becton-Dickinson, San Joes, Calif., USA), and the percent (%) of cells expressing GFP was recorded to evaluate transfection efficiency.

Figure 4A:
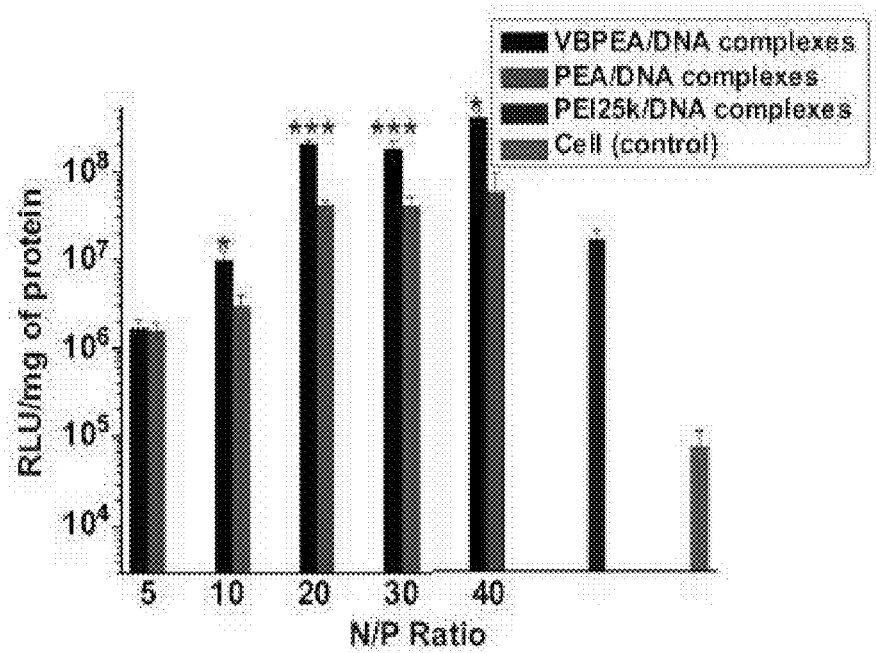
FIGS. 4a to 4c show the results of measuring transfection efficiency by the luciferase analysis of various cells treated with gene delivery complexes prepared at various N/P ratios (5, 10, 20, 30, 40 and 50 N/P) under serum-free conditions.
Figure 4B:
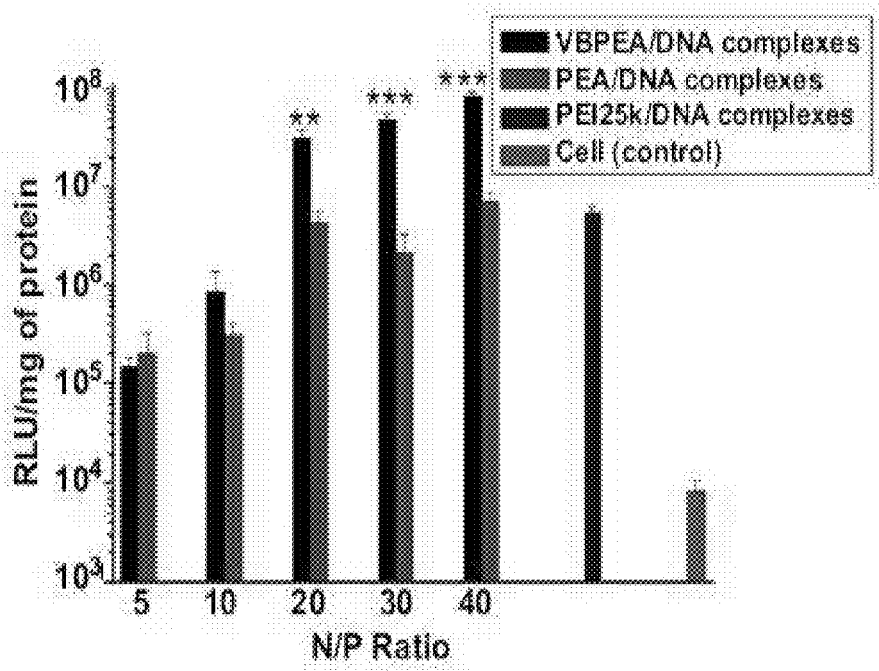
Figure 4C:
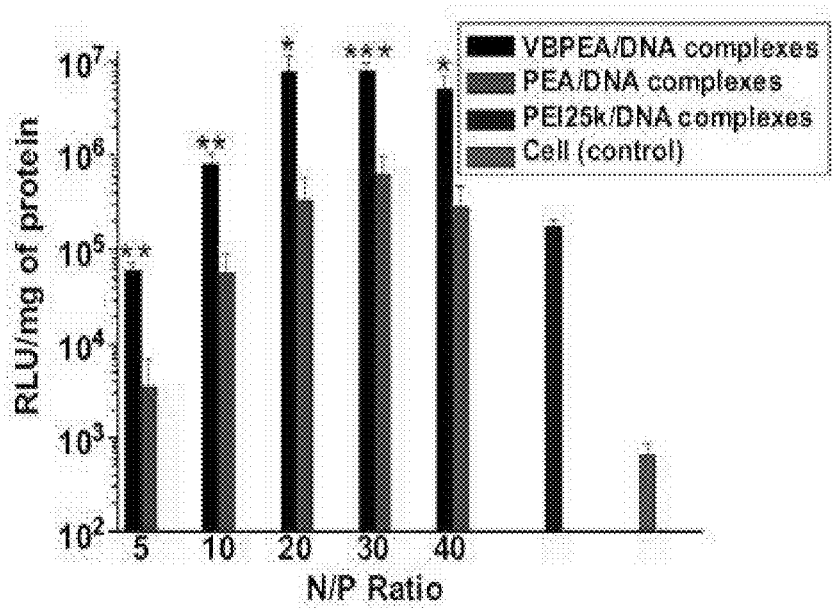
Figure 4D:
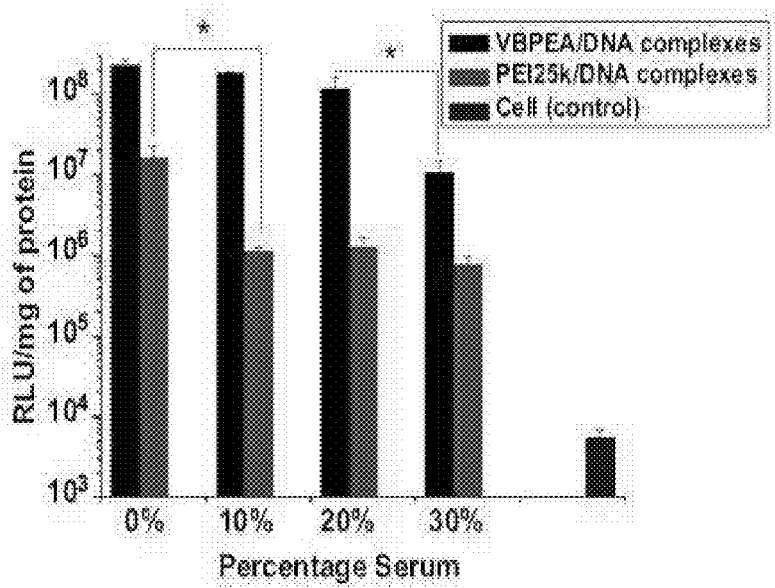
FIG. 4d shows the results of measuring the transfection efficiency of the inventive complex (N/P: 20) by a luciferase assay for A549 cells treated with the inventive complex at a serum concentration of 0, 10, 20 or 30% in order to examine the influence of serum on the stability of the complex.
Figure 4E:
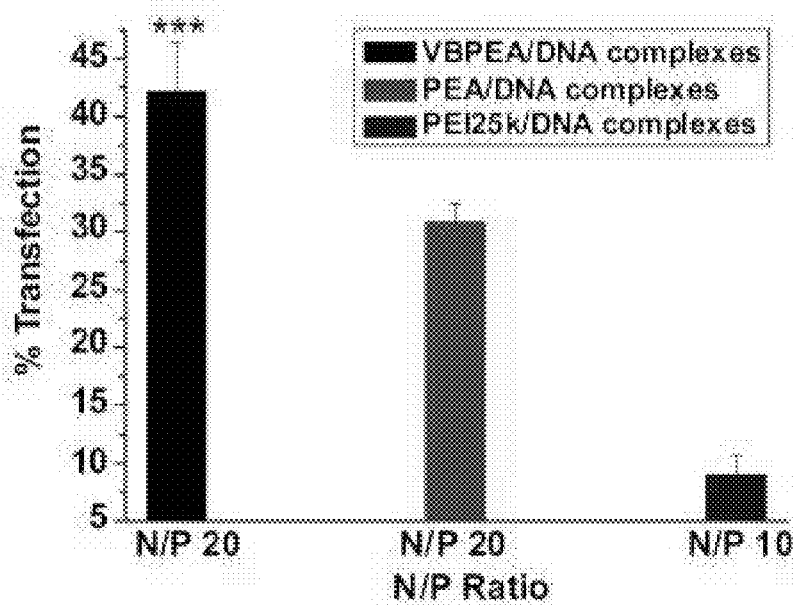
FIG. 4e shows the results of analyzing the GFP expression of VBPEA in A549 cells by flow cytometry in order to examine the in vitro transfection efficiency of the vitamin B6-coupled poly(ester amine) (VBPEA).
Figure 5:
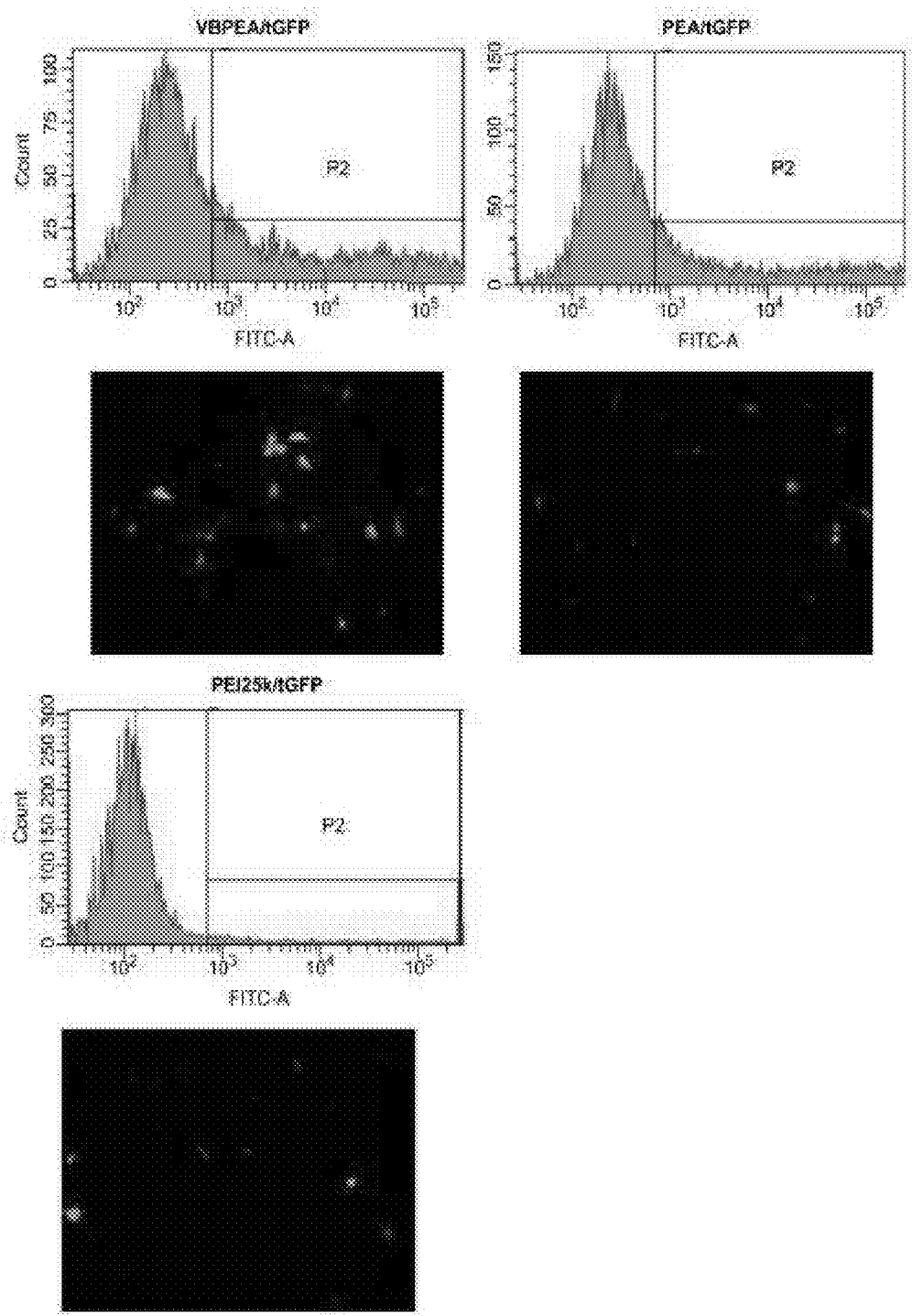
FIG. 5 shows the results of analyzing the GFP expression of VBPEA in A549 cells by flow cytometry in order to examine the in vitro transfection efficiency of the vitamin B6-coupled poly(ester amine) (VBPEA).

As a result, as can be seen in FIGS. 4e and 5, the PEA/DNA complex showed a transfection efficiency of 30-35% and the PEI25k/DNA complex showed a transfection efficiency of 10-13%, whereas the VBPEA/DNA complex showed a transfection efficiency of 40-45%.

5-3. Analysis of In Vivo Biodistribution

The VBPEA/pGL3 complex was injected intravenously into Balb/c mice (4 animal per group), and the in vivo biodistribution of the complex was analyzed. The animals were purchased form Orient Bio Inc. (Korea) and housed in an animal facility at a temperature of 23±2° C. and a relative humidity of 50±20% with 12-hr light/12-hr dark cycles. All the experimental procedures in this study were approved by the Animal Care and Use Committee at Seoul National University (SNU-120409-3).

Specifically, each of VBPEA and PEA was coupled with 30 µg of a pGL3 plasmid at a N/P ratio of 20 and adjusted to a final volume of 100 µl with normal saline. As a control, DNA alone in normal saline was used. Each of the complexes and the control was injected intravenously into the tail veins of 6-week-old Balb/c mice by a 40 U insulin syringe (0.3×8 mm needle, 1 mL). At 4 days after injection of the complexes, the mice of each group were sacrificed by cervical dislocation, and all the organs were extracted. The organs were washed with cold saline, weighed, crushed, suspended in 2.5× cell lysis buffer (Promega, USA) at a concentration of 25%, and homogenized. Then, the suspension was centrifuged at 4° C. at 10,000 rpm for 10 minutes to collect the cell lysate. 100 µl of the cell lysate collected from each sample was subjected to a luciferase assay using a chemiluminometer.

Figure 4F:
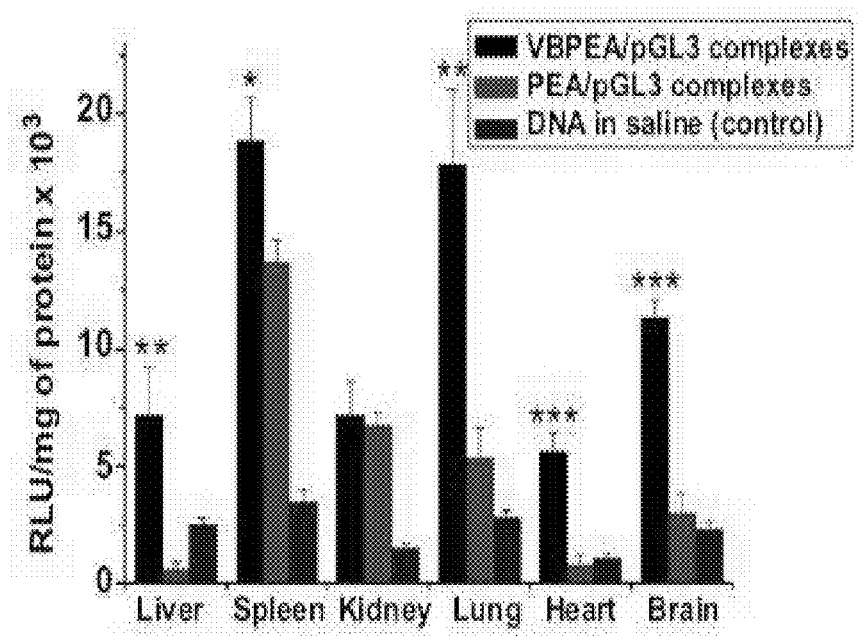
FIG. 4f shows the in vivo biodistribution of the vitamin B6-coupled poly(ester amine) (VBPEA) administered by aerosol delivery.

As a result, it was shown that luciferase activity was higher in the order of the spleen, the lung, the brain, the liver, the kidney and the heart (FIG. 4f). It was found that the cell uptake of the complex of the present invention was promoted by vitamin B6 in the liver, lung and brain in which the expression levels of genes are generally low due to limited uptake of medicaments. Immediately after intravenous injection, the complex showed a tendency to aggregate with blood cells and serum components, indicating that the composite particles were accumulated in the capillary blood vessels of the lung. This is believed to be because the size of the complex particles that were leaked from the blood vessels was 60 nm or more, suggesting that the complex particles did flow out of lung tissue. Slightly greater complex particles were found in liver cells at high concentrations. This is believed to be because the liver metabolizes vitamin B6. Thus, when VBPEA was used, luciferase activity was found in the liver, unlike the use of PEA.

Example 6: Study on Transfection Mechanism of VBPEA

In order to example a mechanism by which the high transfection efficiency of the inventive VBPEA as described in Example 5 is achieved, the following experiment was performed.

6-1. Competitive Inhibition Experiment Using 4'-Deoxypyridoxine

In order to examine the role of vitamin B6 in the transfection of VBPEA of the present invention, a competitive inhibition experiment was performed using 4'-deoxypyridoxine that is a structural analogue of vitamin B6. Specifically, A549 cells cultured to a confluence of 80% were treated with 0, 1, 2, 5, 10 or 20 mM of 4'-deoxypyridoxine and treated with the VBPEA/DNA or PEA/DNA complex for 10 minutes. After 24 hours, the cells were collected and subjected to an in vitro luciferase assay.

Figure 6:
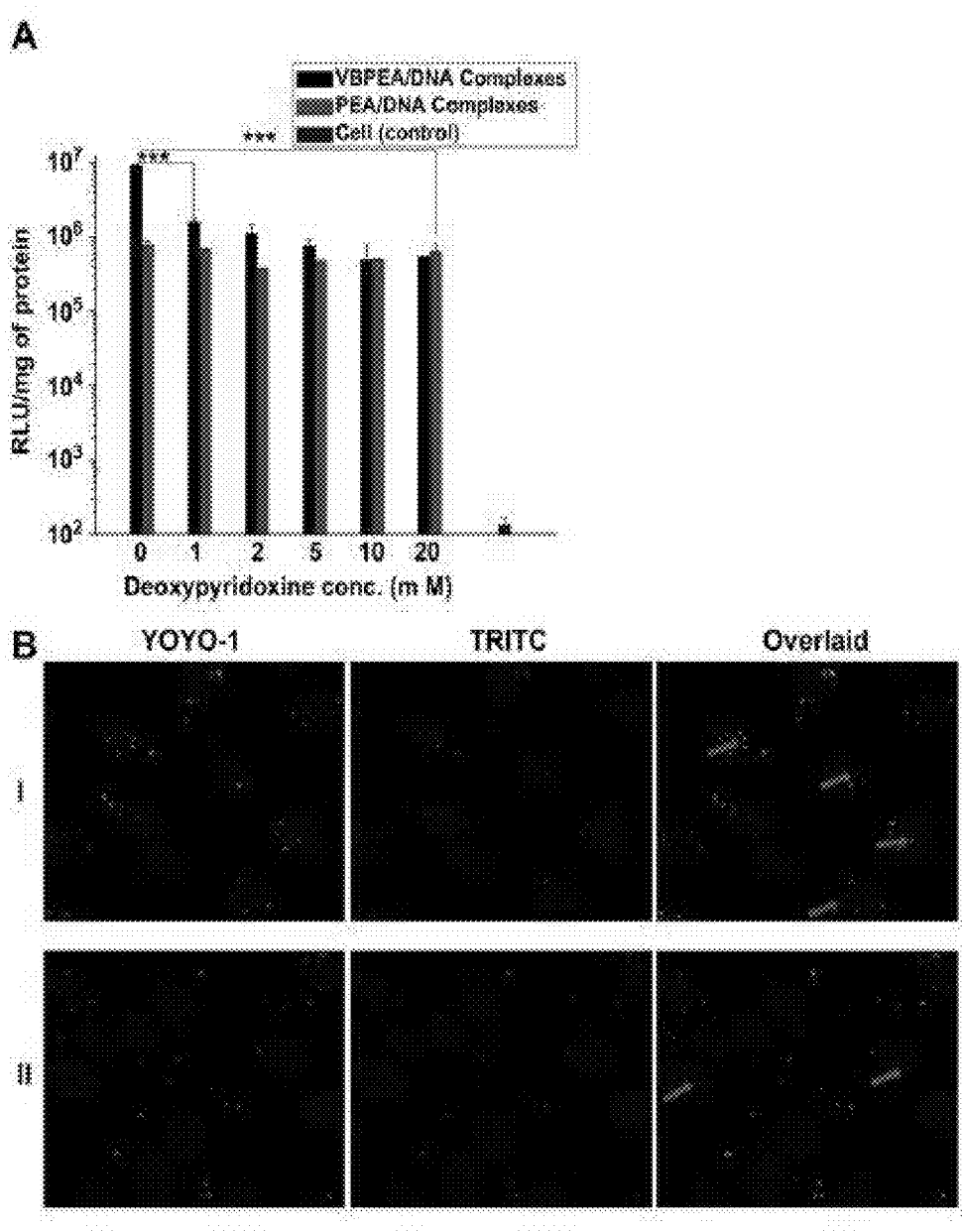
FIG. 6 shows the results of analyzing transfection efficiency after treatment with 4'-deoxypyridoxine (a structural analogue of vitamin B6) in order to analyze the mechanism of transfection of the vitamin B6-coupled poly(ester amine) (VBPEA).
Figure 8A:
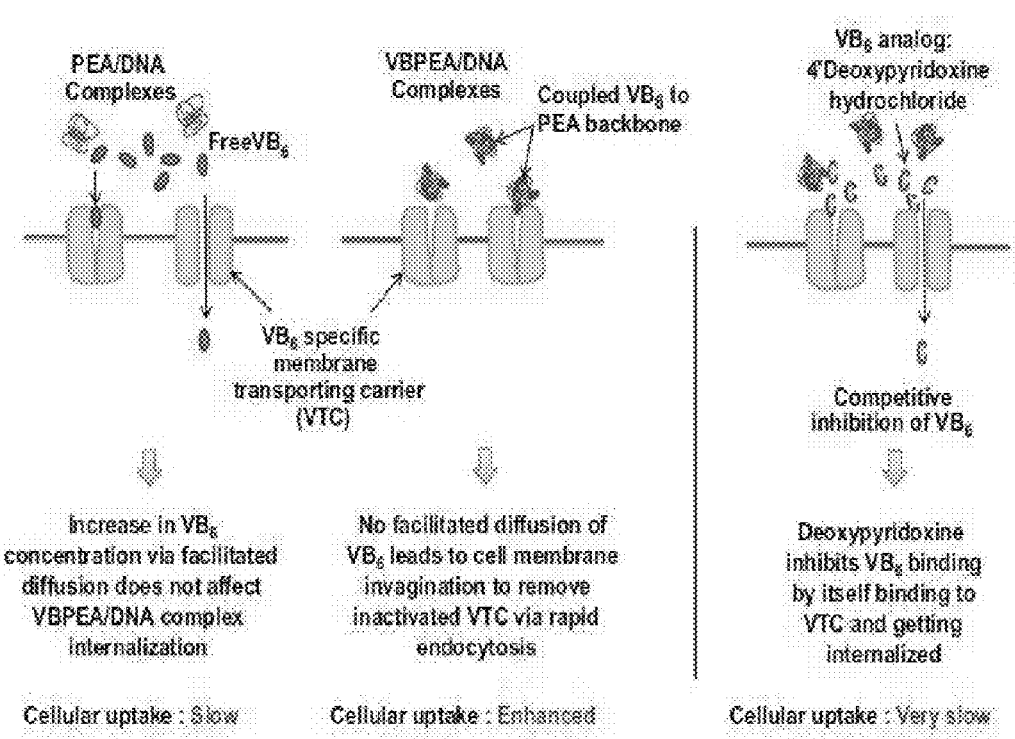
FIG. 8a schematically shows the influence of vitamin B6 on the transfection of the vitamin B6-coupled poly(ester amine) (VBPEA).
Figure 8B:
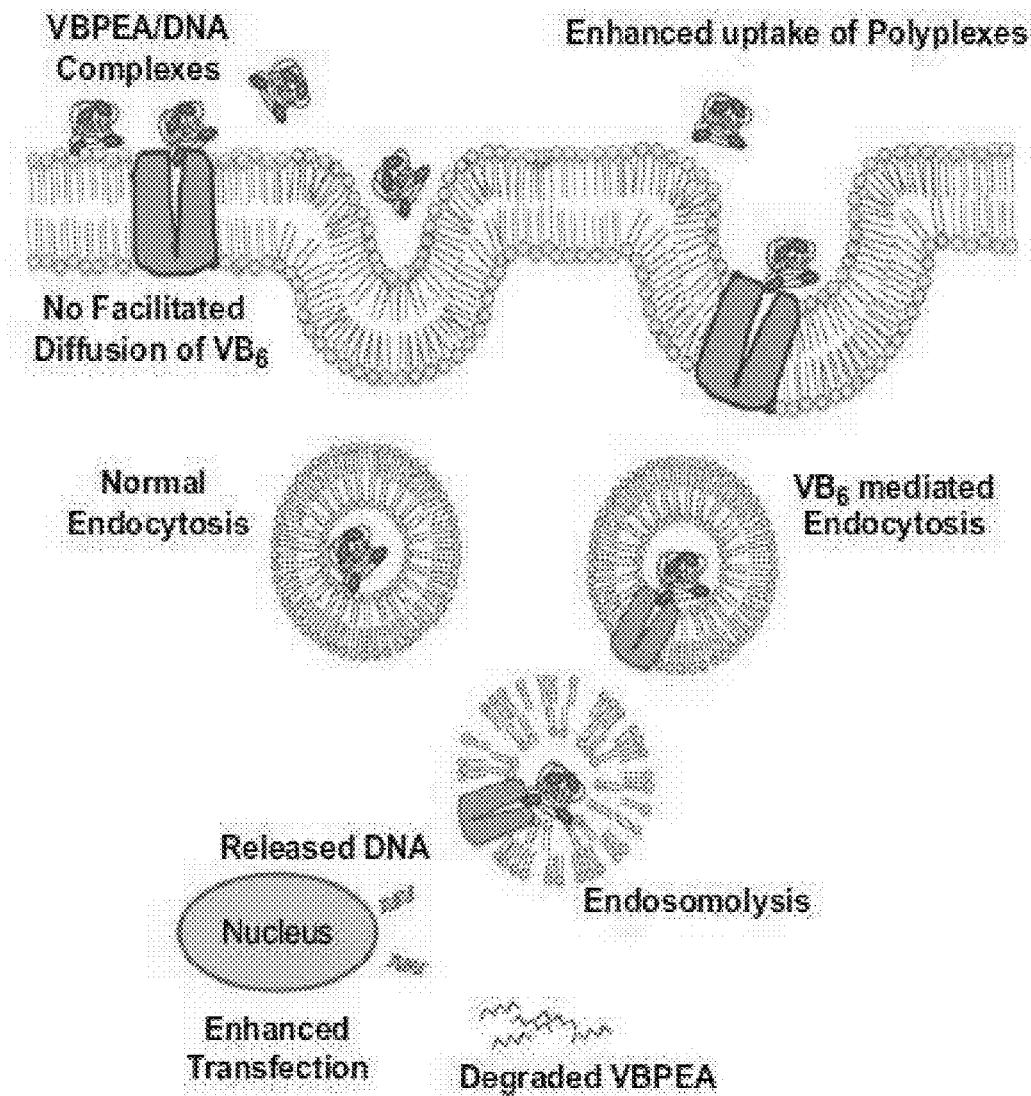
FIG. 8b schematically shows the mechanism of transfection of the vitamin B6-coupled poly(ester amine) (VBPEA).

As shown in FIG. 6A, when the cells were treated with 4'-deoxypyridoxine (1 mM) that is a structural analogue of vitamin B6, the transfection efficiency of the VBPEA/DNA complex significantly decreased to that of the PEA/DNA complex. This suggests that the high transfection efficiency of the VBPEA/DNA complex occurs because vitamin B6 binds to VTC (VB6 transporting membrane carrier). In other words, this suggests that the vitamin B6 of VBPEA increases the accessibility of the VBPEA/DNA complex to the cell membrane through VTC to thereby increase the transfection efficiency of the complex.

6-2. VBPEA Inhibition Experiment Using Confocal Microscope

The signal of TRITC-labeled VBPEA and YOYO-1-labeled DNA in the intracellular trafficking of A549 cells was observed with an inverted laser scanning confocal microscope (Zeiss LSM 710, Carl Zeiss) in the presence or absence of 4'-deoxypyridoxine.

Specifically, TRITC (25 µl, 1 mg/100 µl DMF) was added to VBPEA (1 ml, 10 mg/mL $H_2O$) (blocked about 1% of total amine) and stirred overnight. Unreacted TRITC was removed by washing three times with ethyl acetate (2 mL), and the remaining material was freeze-dried and resuspended in water. pDNA (1 µg) was labeled with YOYO-1 iodide (2 µl, 1 mM in DMSO) by stirring these materials in a dark place at 25±1° C. for 2 hours. It was stored at −20° C. A549 cells were seeded into each well of a 6-well culture dish at a density of $2 \times 10^5$ cells/well and transfected with the double-labeled VBPEA/DNA in the presence or absence of 4'-deoxypyridoxine. After 120 minutes, the cells were washed three times with 1×PBS, and then fixed with 4% paraformaldehyde at 4° C. for 10 minutes. The nuclear DNA was counter-stained with DAPI, and the cells were imaged with a confocal microscope.

As a result, as described in Example 6-1, the confocal microscope images showed that the VBPEA/DNA complex of the present invention reduced the accessibility of VBPEA to VTC in the presence of 4'-deoxypyridoxine, and thus the cell uptake thereof significantly decreased (FIG. 6B).

6-3. Analysis of Influence of Free or Coupled Vitamin B6 on Gene Transfection

In order to analyze the influences of vitamin B6 alone and VBPEA on the promotion of transfection, the following experiment was performed.

Specifically, A549 cells were treated with 0, 5, 20, 50 or 100 µM of vitamin B6 together with a PEA/pGL3 plasmid complex (N/P: 20), and the transfection efficiency of the PEA/pGL3 plasmid complex was compared with that of a VBPEA/pGL3 plasmid complex (N/P: 20).

As a result, as can be seen in FIG. 7A, the VBPEA/DNA complex showed high transfection efficiency compared to the PEA/DNA complex used together with free vitamin B6, and the PEA/DNA complex did not show a significant difference in transfection efficiency even when the concentration of free vitamin B6 increased. This suggests that the transfection of PEA is achieved by a mechanism separate from free vitamin B6.

6-4. Analysis of the Ability of VBPEA to Bind to Cancer Cells and Normal Cells

Mouse primary lung cells were seeded into a 24-well culture dish at a concentration of $1 \times 10^5$ cells/well, and then washed with PBS and transfected with the VBPEA/DNA complex (N/P: 20) under serum-free conditions. After 3 hours, the medium was replaced with DMEM/F-12 complete medium. Similarly, human lung adenocarcinoma LA-4 cells, human lung adenocarcinoma A549 cells and human bronchial epithelial 16HBE cells were also transfected. After 24 hours, the degree of luciferase expression was analyzed and compared between the normal cells and the cancer cells. In addition, in order to verify that the VBPEA/DNA complex is not toxic in normal cells, an MTT assay was performed in the same manner as described above.

As a result, as can be seen in FIG. 7B, the transfection efficiency of the VBPEA/DNA complex was significantly higher in human or mouse lung cancer cells (A549 cells and LA-4 cells) than in human or mouse primary lung cells. This indicates that VBPEA/DNA is highly efficiently internalized into cancer cells compared to normal cells, because the requirement for vitamin B6 is high in cancer cells whose growth and proliferation actively occur. Meanwhile, it was shown that the VBPEA/DNA complex of the present invention showed no toxicity in normal cells (FIG. 10).

6-5. Comparison of Endocytosis Mechanism Between PEA and VBPEA

In order to examine the VBPEA uptake pathway, various endocytosis pathways were inhibited, and then the comparison of transfection efficiency was performed. To study clathrin-mediated endocytosis, A549 cells were treated with 1, 2 and 3 μg/mL of chlorpromazine for about 1 hour, and then the VBPEA/DNA complex (N/P: 20) was added thereto. Similarly, the caveolae-mediated uptake was inhibited by treatment with 2.5, 6.5 or 10 mg/mL of its inhibitor β-methyl cyclodextrin or 100, 200 or 300 μM of genistein. After treatment with the inhibitors for 1 hour, the A549 cells transfected, and after 24 hours, the expression of luciferase was measured.

Figure 11A:
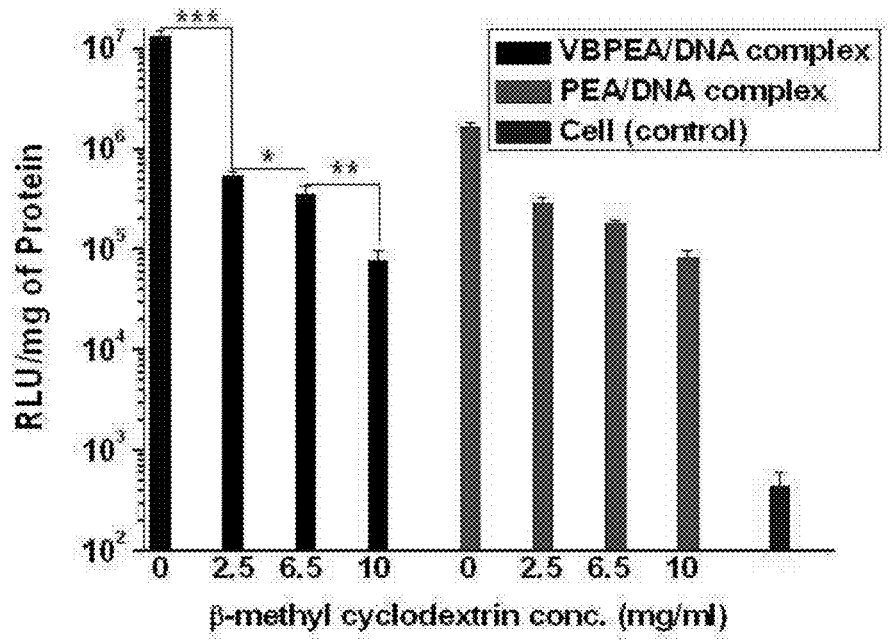
FIGS. 11a to 11c show the results of comparing transfection efficiency after inhibition of various endocytosis pathways in order to examine the uptake pathway of VBPEA. Specifically, caveolae-mediated uptake was inhibited by treatment with its inhibitor β-methyl cyclodextrin (FIG. 11a) or genistein (FIG. 11b), and clathrin-mediated endocytosis was inhibited by treatment with its inhibitor Chlorpromazine (FIG. 11c) (n=3, error bar=SD) (*p<0.05; p<0.01, *p<0.001, one-way ANOVA).
Figure 11B:
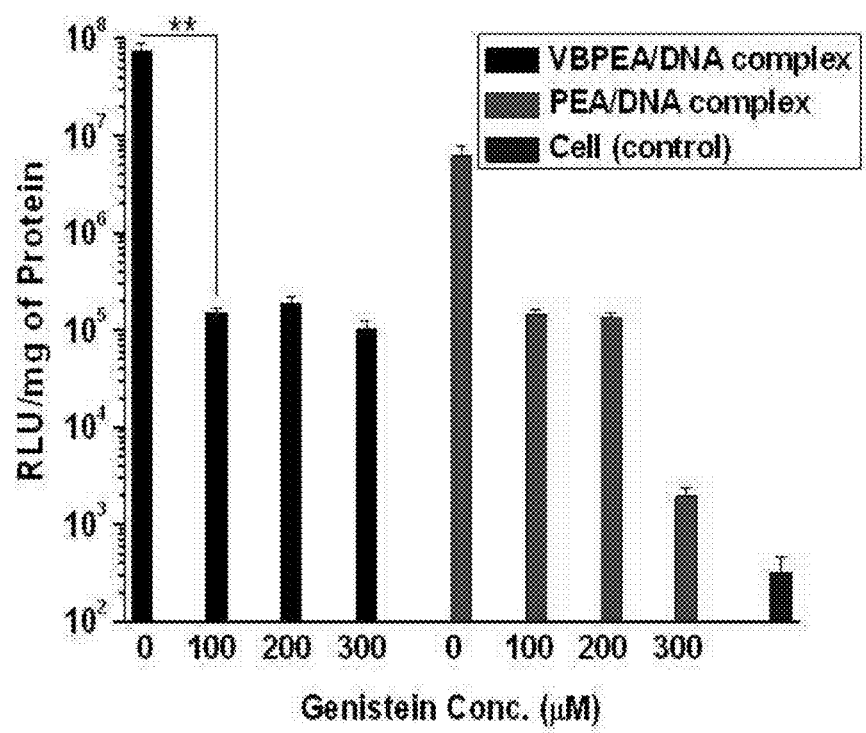
Figure 11C:
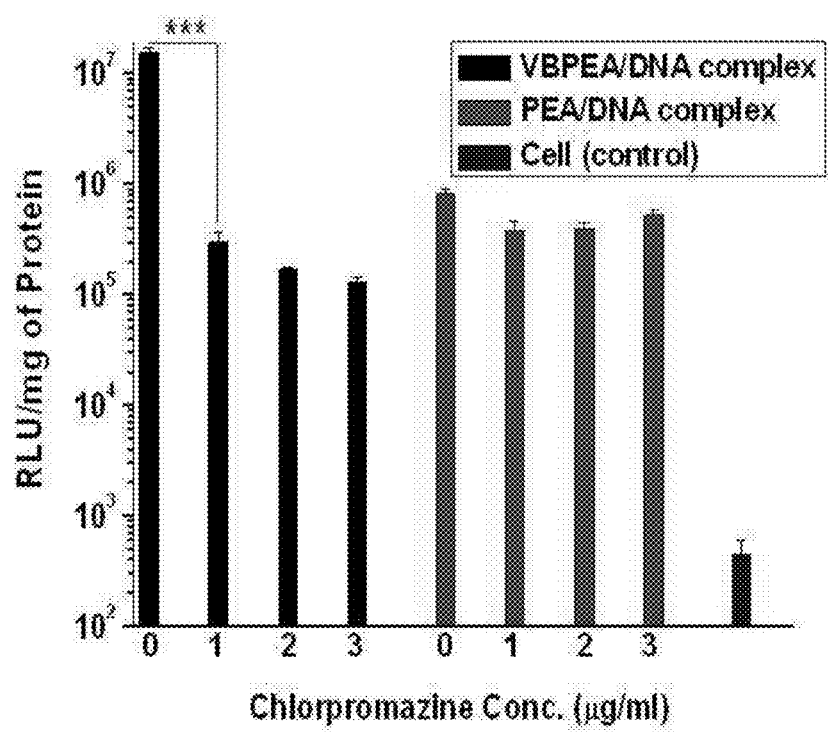

It was shown that, when the cells were treated with the caveolar inhibitors β-methyl cyclodextrin and genistein, the VBPEA-mediated or PEA-mediated transfection efficiency decreased in a concentration-dependent manner. This suggests that the two gene carriers use the caveolar uptake pathway. On the other hand, the inhibition of clathrin-mediated endocytosis by chlorpromazine reduced the transfection efficiency of the VBPEA/DNA complex, but did not change the transfection efficiency of the PEA/DNA complex (FIG. 11). This suggests that, in transfection with PEA, no transporter is involved, and thus clathrin-mediated endocytosis does not occur, whereas in transfection with VBPEA, clathrin-mediated endocytosis occurs due to the involvement of vitamin B6 transporter.

6-6. Examination of Proton Sponge Effect of PEI in VBPEA

It is known that the relatively high transfection effect of PEI is attributable to its ability to escape from endosomes by the proton sponge effect. It is known that this effect is because PEI acts as a buffer during the acidification of endosomes by the introduction of protons and Cl⁻ and the resulting swelling and hemolysis of endosomes. In order to examine whether the vitamin B6-coupled poly(ester amine) (VBPEA) according to the present invention also has the same proton sponge effect, and the buffer ability of the VBPEA was examined.

Specifically, A549 cells were seeded into a 24-well plate at a density of $1.0 \times 10^5$ cells/well and cultured to a confluence of 80%, and then cultured for 10 minutes in serum-free medium supplemented with the endosome proton pump inhibitor bafilomycin A1 (vacuolar type H⁺ ATPase specific inhibitor, 200 nM) diluted in DMSO. Then, the cells were treated with each of the VBPEA/DNA complex (N/P: 20) of the present invention and PEI25K/DNA (N/P: 10) as a control, and after 24 hours, the expression of luciferase was measured in the same manner as described above.

Figure 12:
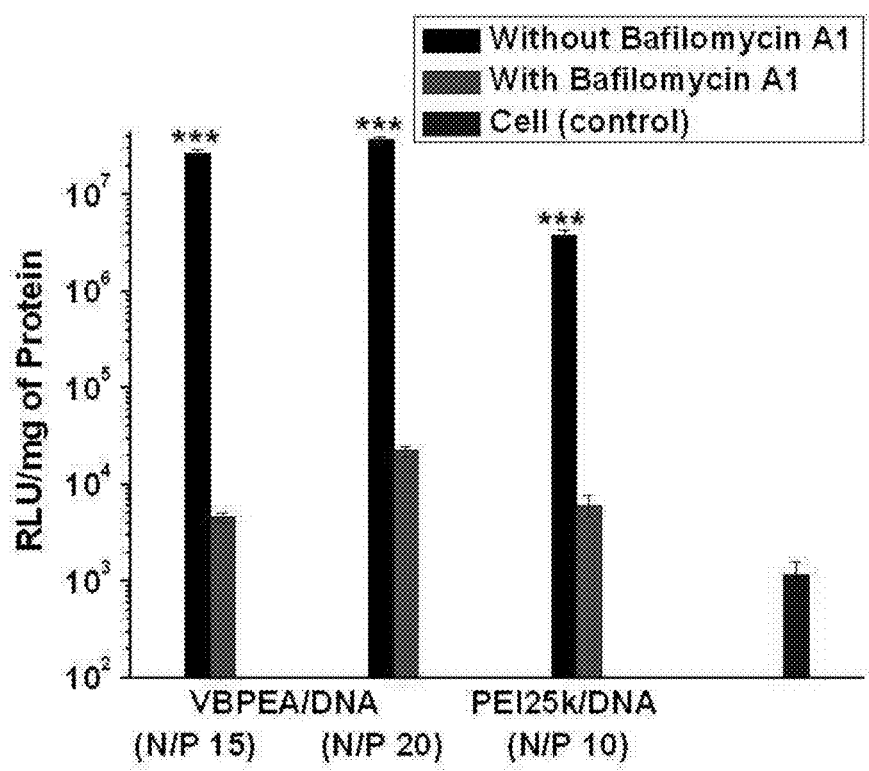
FIG. 12 shows the results of treating cells with bafilomycin A1 (vacuolar type $H^+$ ATPase specific inhibitor, 200 nM) which is an endosome proton pump inhibitor, in order to examine whether the vitamin B6-coupped poly(ester amine) (VBPEA) has a transfection mechanism caused by the proton sponge effect (n=3, error bar=SD) (***p<0.001, one-way ANOVA).

When the vacuolar-type proton pump was inhibited with bafilomycin A1 as described above, transfection with VBPEA decreased by about 1000 times. This suggests that the transfection of VBPEA is promoted by the acidification of endosomes (FIG. 12). The inhibitor prevented the acidification of endosomes and inhibited bursting for release of the gene carrier.

Example 7: Silencing with VBPEA 7-1. Efficiency of siRNA with VBPEA

In order to examine whether the use of the VBPEA gene carrier of the present invention makes gene silencing possible, an experiment on the transfection of siRNA was performed.

Specifically, A549 cells were transfected with a Lipofectamine™/pGL3 plasmid complex under serum-free conditions, and after 3 hours, the medium was replaced, and the cells were treated with a VBPEA/siLuc (si Luciferase) or siScr (si Scrambled) complex or a PEA/siLuc or siScr complex (N/P: 20). Herein, the siRNAs were used at a concentration of 50, 75, 100 or 150 μM. The cells were additionally cultured for 3 hours, and then the medium was replaced with 10% serum-containing complete medium. After 24 hours, the expression of luciferase was measured by the same luciferase assay as described above and was normalized to protein concentration. Luciferase silencing efficiency was calculated relative to the luciferase level of control cells not treated with the luciferase-specific siRNA.

As a result, silencing efficiency by the VBPEA/siLuc complex increased by 94% compared to that in the use of the PEA/siLuc complex. Silencing activity was stabilized when the concentration of siRNA was 100 μM higher. The use of the gene carrier/non-specific Scrambled siRNA (siScr, control) complex or the use of the siLuc plasmid alone showed an insignificant silencing effect (FIG. 7c).

7-2. Measurement of Cytotoxicity of siRNA with VBPEA

An MTT assay showed that the VBPEA/siLuc complex had no cytotoxicity. Specifically, the cytotoxicity of the VBPEA/siRNA or PEA/siRNA complex (N/P: 20) comprising various concentrations (50, 100 and 150 μM) of siRNA was measured in A549 cells. After 36 hours, an MTT assay was performed in the same manner as described above.

Figure 13:
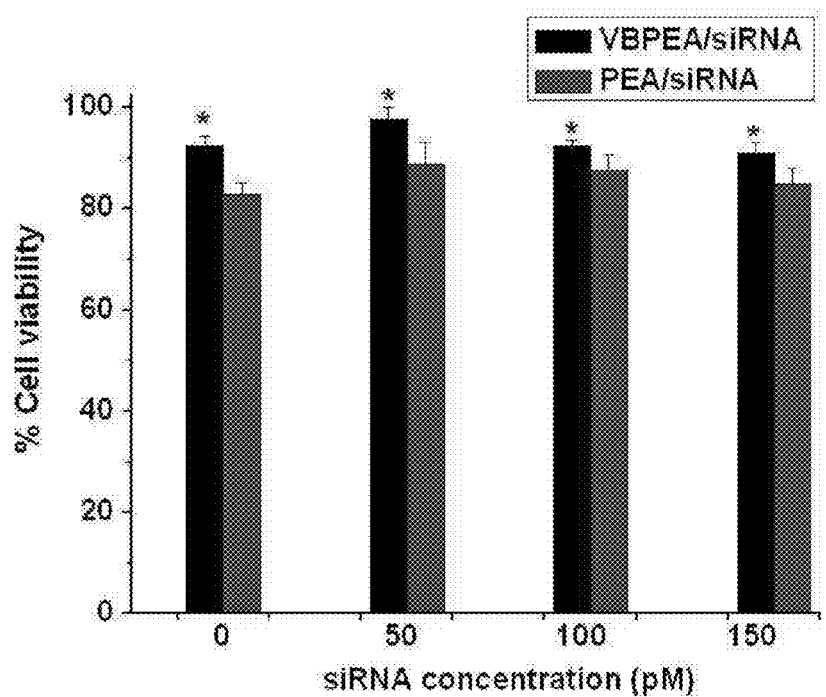
FIG. 13 shows the results of examining the cytotoxicity of a gene delivery complex coupled to siRNA (n=3, error bar=SD) (*p<0.05, one-way ANOVA).

As a result, it was shown that the VBPEA-mediated gene silencing of the VBPEA/siRNA complex was improved due to low cytotoxicity compared to that of the control (PEA/siRNA) (FIG. 13). Such results suggest that VBPEA can be effectively used for the silencing of vitamin B6-dependent enzymes that are involved in cancer cell proliferation, indicating that it can be use as an anticancer agent.

Example 8: Effect of VBPEA-Mediated Gene Silencing on Inhibition of Cancer Cell Proliferation As confirmed in Example 7, the use of the VBPEA of the present invention efficiently caused gene silencing. Accordingly, it was believed that the VBPEA would be particularly efficient for silencing of vitamin B6-dependent enzymes, and based on the fact that vitamin B6 can play as an important coenzyme in cancer cell proliferation, the effect of VBPEA-mediated gene silencing on cancer cell proliferation was examined.

8-1. Measurement of Serine Hydroxymethyltransferase Silencing Efficiency

Figure 14A:
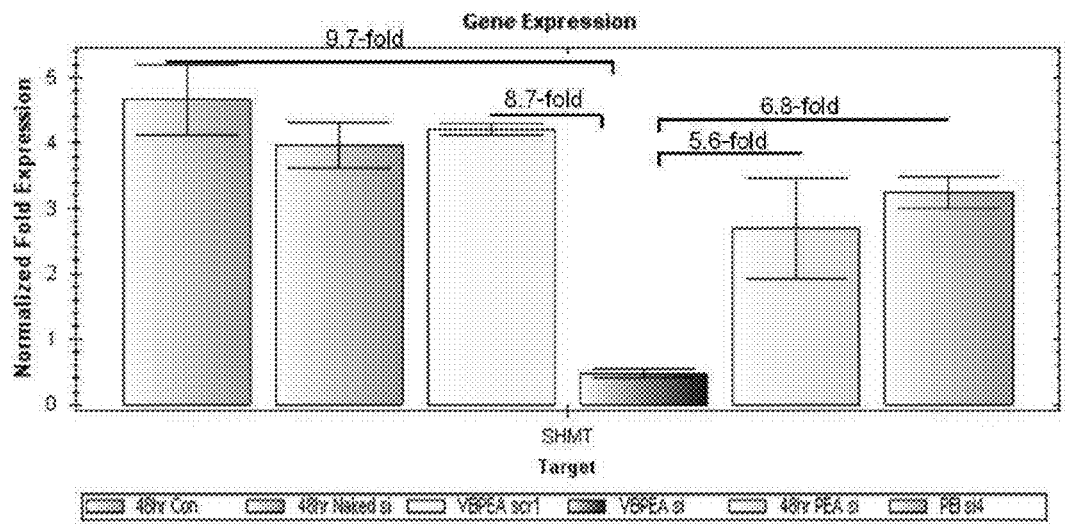
FIGS. 14a and 14b show the results of examining whether gene silencing is efficiently induced by the inventive gene delivery complex coupled with siRNA.
Figure 14B:
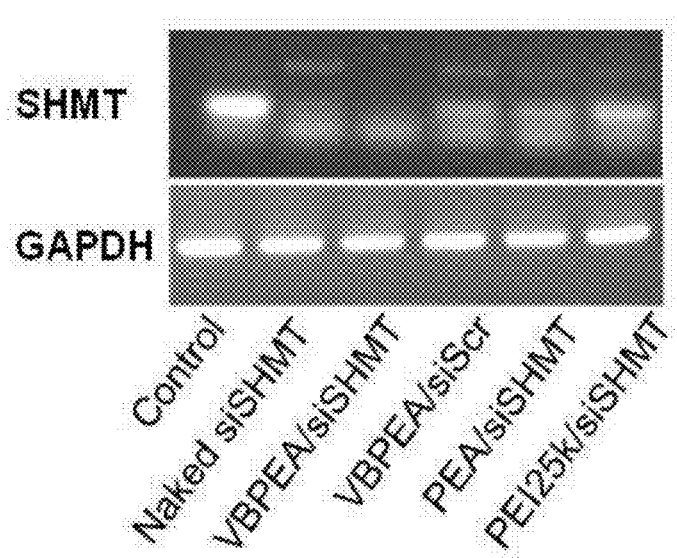

First, using esiRNA (esiRNA Human SHMT1, Sigma, Cat No: EHU159081-50UG)) against serine hydroxymethyltransferase (SHMT) that is a vitamin B6-dependent enzyme playing an important role in cancer cell proliferation, the gene silencing efficiency of VBPEA was analyzed by real time-qPCR and reverse transcriptase (RT)-PCR (FIG. 14b).

As a result, it was shown that the gene silencing efficiency of VBPEA was significantly higher than those of other control gene carriers. Specifically, the expression of the SHMT gene decreased by 9.7 times in the use of VBPEA compared to the negative control, 6.8 times in the use of PEI25k, and 5.6 times in the use of PEA (FIGS. 14a and 14b).

8-2. Measurement of Cancer Cell Death Induction

Whether the VBPEA-mediated silencing of SHMT gene in cancer cells induces cell death was examined. As siSHMT for silencing the SHMT gene, esiRNA human SHMT1 (Sigma Aldrich, Cat No: EHU159081-50UG) was used.

Specifically, A549 cells were treated with VBPEA/siSHMT, PEA/siSHMT or VBPEA/siScr, and a positive or negative control group was prepared. DNA cleavage that is the characteristic of cell death was analyzed by green fluorescence (fluorescence-dUTP), and cell death was measured by a TUNEL assay (FIG. 15).

Figure 15:
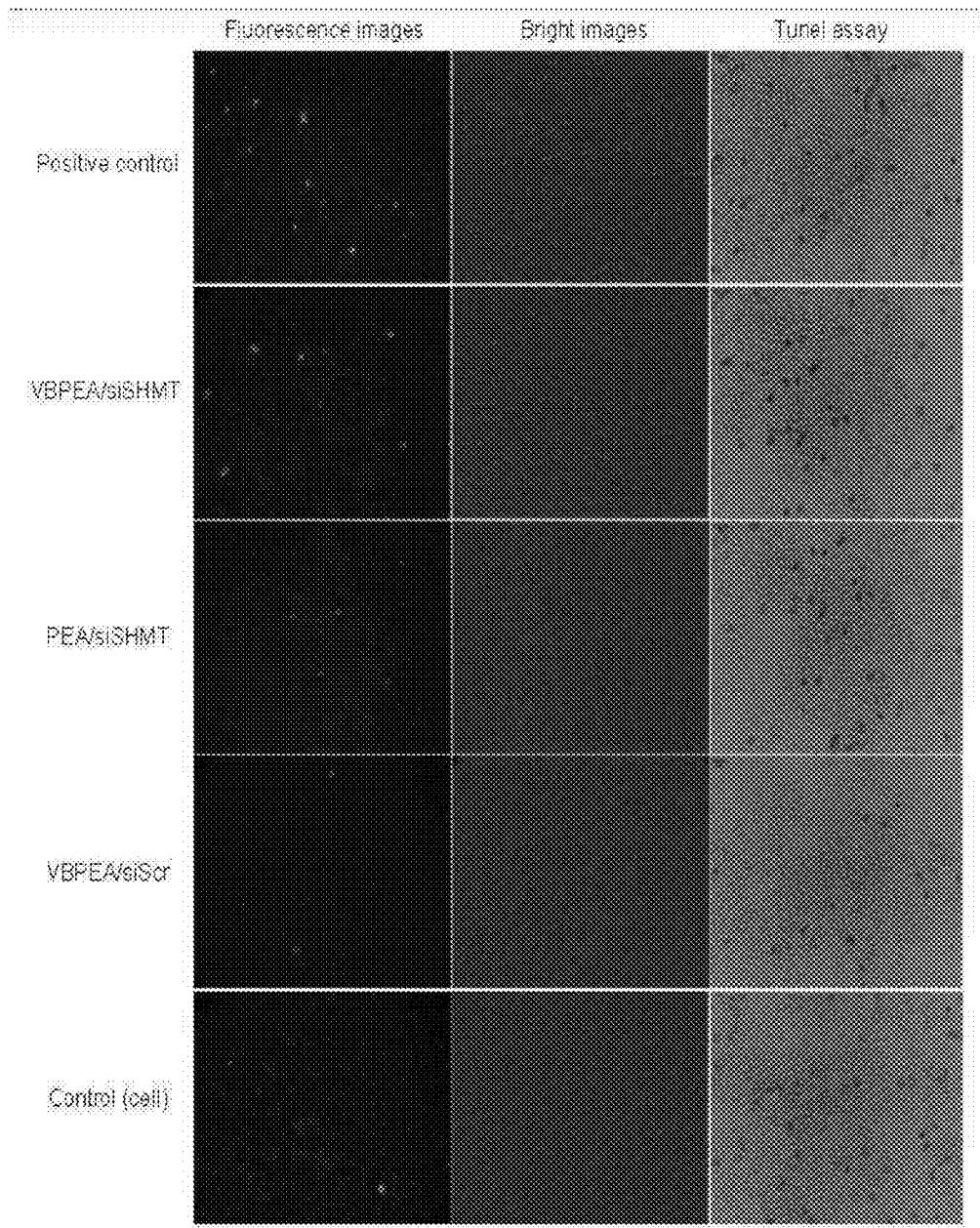
FIG. 15 shows the results of microscopic observation conducted to examine whether gene silencing is efficiently induced by the inventive gene delivery complex coupled with siRNA.

As a result, as can be seen in FIG. 15, the frequency of cell death was significantly high in cells treated with VBPEA/siSHMT.

8-3. Measurement of Inhibitory Effect on Cancer Cell Proliferation

Whether the VBPEA-mediated silencing of the SHMT gene in cancer cells has an inhibitory effect on cancer cell proliferation was examined. Specifically, A549 cells were treated with VBPEA/siSHMT, PEA/siSHMT or VBPEA/siScr, and an untreated negative control group was prepared. The proliferation of the cells was measured over 0-4 days. The proliferation rate of the cells was analyzed by a WST assay (FIG. 16).

The WST assay uses a mechanism in which tetrazolium salt WST-1 is cleaved to formazan by mitochondrial dehydrogenase having activity in living cells. In this assay, the concentration of formazan that is produced only in viable cells is determined by measuring the absorbance at 450 nm, thereby determining the number of viable cells.

Figure 16:
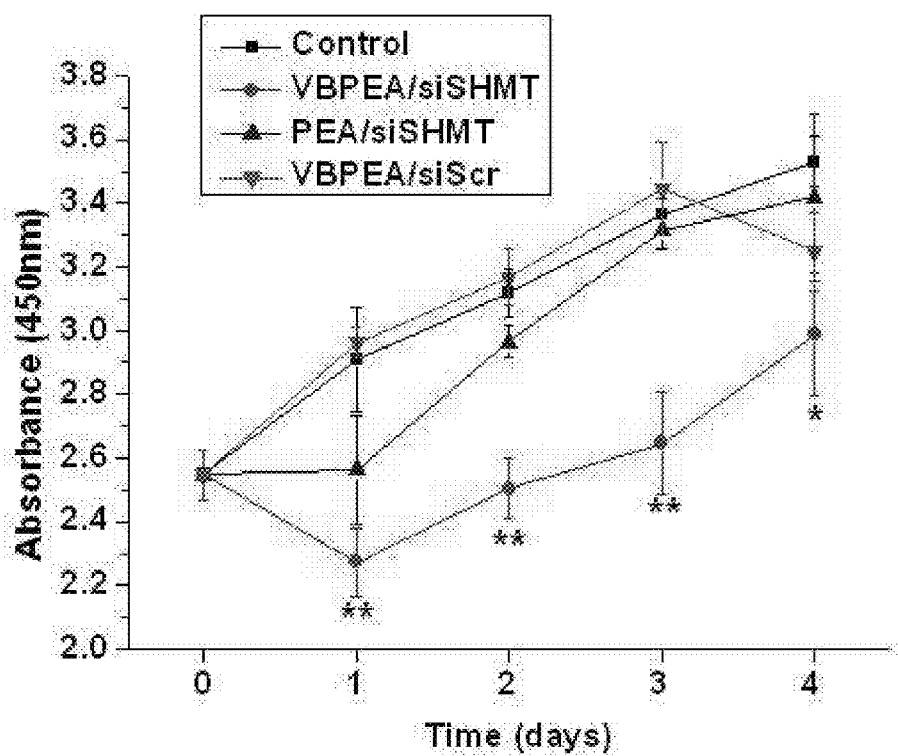
FIG. 16 shows the inhibition of cancer cell proliferation by siSHMT delivered to cancer cells by the inventive gene delivery complex.

As a result, as can be seen in FIG. 16, the proliferation of the cells treated with VBPEA/siSHMT was significantly inhibited compared to that of the cells treated with PEA/siSHMT or VBPEA/siScr. Particularly, on days 1 and 2, the cancer cells did not proliferate, and the number of the cells was smaller than the original cell number due to the cell death effect of VBPEA/siSHMT.

Example 9: Examination of Effect of VBPEA-Mediated Gene Silencing on Inhibition of Cancer Cells Proliferation in Animal Model As shown in Example 8, the use of the VBPEA of the present invention induced silencing of the cancer-related gene (serine hydroxymethyltransferase (SHMT)) and showed an inhibitory effect on cancer cell proliferation in the in vitro experiment. Accordingly, the inhibitory effect of VBPEA-mediated gene silencing on cancer cell proliferation was examined by an in vivo experiment in a cancer-induced animal (mouse) model.

9-1. Construction of Cancer-Induced Animal Model and Therapeutic Method

Human lung adenocarcinoma A549 cells ($3 \times 10^6$ cells, 100 µl) that stably express luciferase were injected subcutaneously into 5-week-old male nude mice (Balb/c, 4 animals per group) to construct a cancer-induced animal model. The animals were purchased from Orient Bio Inc. (Korea) and housed in an animal facility at a temperature of $23 \pm 2°$ C. and a relative humidity of $50 \pm 20\%$ with 12-hr light/12-hr dark cycles. All the experimental procedures in this study were approved by the Animal Care and Use Committee at Seoul National University (SNU-120409-3).

One month after injection with the A549 cells, the tumor volume reached about 800-1000 $mm^3$, and then cancer treatment with siSHMT was initiated.

Specifically, a solution of the VBPEA/siSHMT (30 µg) complex (N/P: 20), the PEA/siSHMT complex (N/P: 20) or the PEI25k/siSHMT complex (N/P: 10) in saline was administered to the animals at 48-hour intervals for one month. As a negative control, an empty vector, siSHMT gene (naked siSHMT) or VBPEA/siScr was administered.

During one month of the administration, the tumor size was measured using IVIS Imaging system 100 (Xenogen), and after one month, the animal were sacrificed and the expression level of SHMT protein in the tumor tissue was measured.

9-2. Measurement of Expression Level of SHMT in Cancer Tissue

The expression level of SHMT in the cancer tissue extracted from mice sacrificed in Example 9-1 was measured by Western blotting.

Specifically, the mice of each group were sacrificed by cervical dislocation, and the cancer tissue was extracted. The organs were washed with cold saline, weighed, crushed, suspended in 2.5× cell lysis buffer (Promega, USA) at a concentration, and homogenized. Then, the suspension was centrifuged at $4°$ C. at 10,000 rpm for 10 minutes to collect the cell lysate. The concentration of protein in the cell lysate was measured, and 25 µg of the protein was separated by SDS-PAGE and transferred to a nitrocellulose membrane, followed by immunoblotting (FIG. 17).

Figure 17:
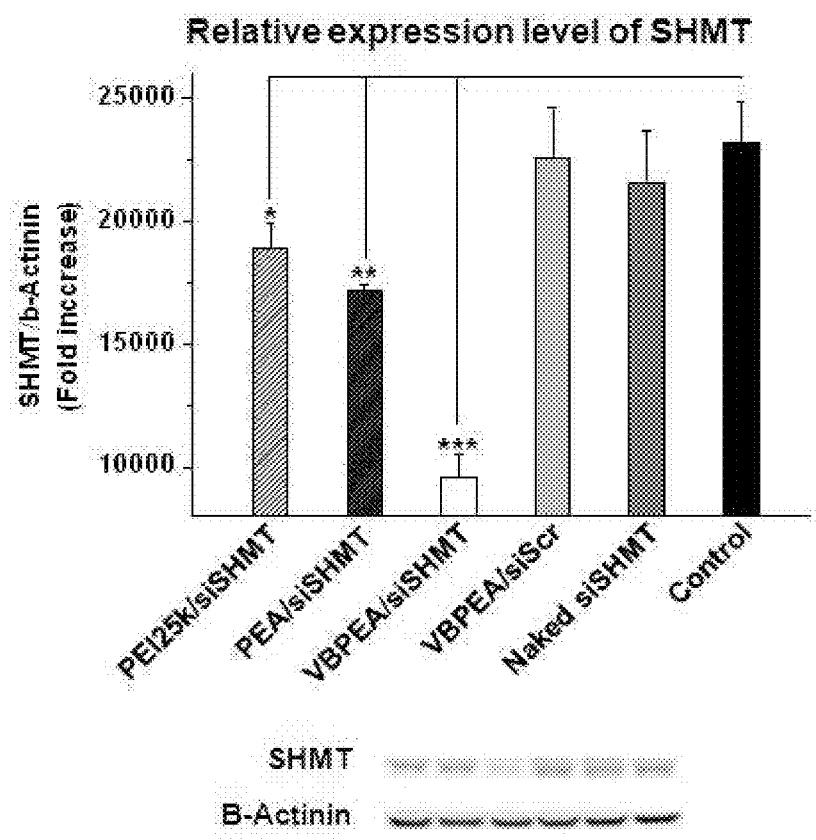
FIG. 17 shows the results of examining the SHMT gene silencing effect of siSHMT delivered by VBPEA in an in vivo experiment in a cancer-induced animal model (n=4 per group).

As a result, as can be seen in FIG. 17, treatment with the VBPEA/siSHMT complex showed an excellent effect on the inhibition of SHMT expression compared to treatment with the PEA/siSHMT or PEI25k/siSHMT complex (FIG. 17).

9-3. Measurement of Tumor Volume

During one month of administration in Example 9-1, the tumor volume was measured once a week using IVIS imaging system 100 (Xenogen). The tumor volume was calculated using the following equation:

Tumor volume ($mm^3$)=$0.5 \times a \times b^2$ wherein a is the smallest diameter, and b is the longest diameter.

Figure 18:
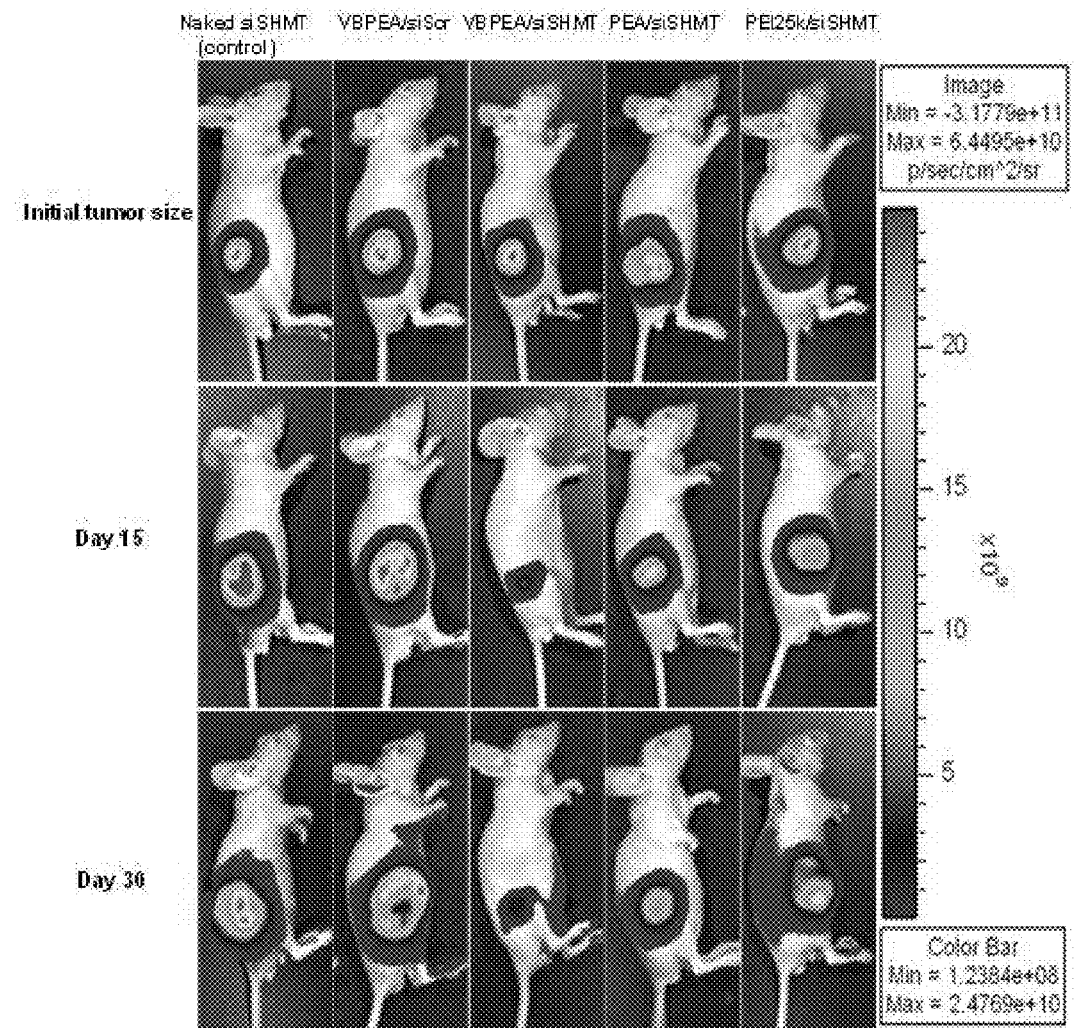
FIG. 18 shows bioluminescence images measured at two-week intervals using IVIS imaging system 100 in an in vivo experiment in a cancer-induced animal model (n=4 per group) in order to determine the change in tumor volume by siSHMT delivered by VBPEA.

The results of measurement using the IVIS imaging system 100 are shown in Table 3 below and FIG. 19, and bioluminescence images measured at 2-week intervals are shown in FIG. 18.

TABLE 3

Results of tumor volume measurement with vernier caliper during administration (1-week intervals)

| Period of administration | Untreated group (mm³) | naked siSHMT (mm³) | VBPEA/ siScr (mm³) | VBPEA/ siSHMT (mm³) | PEA/ siSHMT (mm³) | PEI/ siSHMT (mm³) |
|---|---|---|---|---|---|---|
| Before administration | 961.4 ± 24.7 | 889.4 ± 38.4 | 1000.5 ± 31.8 | 1066.6 ± 31.1 | 1138.4 ± 40.5 | 1166.4 ± 40.5 |
| 1 week | 2016.5 ± 66.4 | 1608.2 ± 69.5 | 1846.0 ± 85.6 | 956.3 ± 52.9 | 1241.9 ± 93.9 | 1203.6 ± 76.9 |
| 2 weeks | 2740.8 ± 49.2 | 2282.8 ± 68.6 | 2794.8 ± 20.7 | 802.1 ± 79.0 | 1283.5 ± 56.5 | 1405.9 ± 56.1 |
| 3 weeks | 3662.0 ± 49.2 | 3187.1 ± 60.9 | 3593.7 ± 51.6 | 590.5 ± 45.6 | 1488.4 ± 64.9 | 1583.5 ± 45.0 |
| 4 weeks | 4428.9 ± 66.6 | 4397.7 ± 53.2 | 4763.0 ± 173.2 | 471.5 ± 25.0 | 1504.6 ± 14.1 | 1884.9 ± 77.1 |

Figure 19:
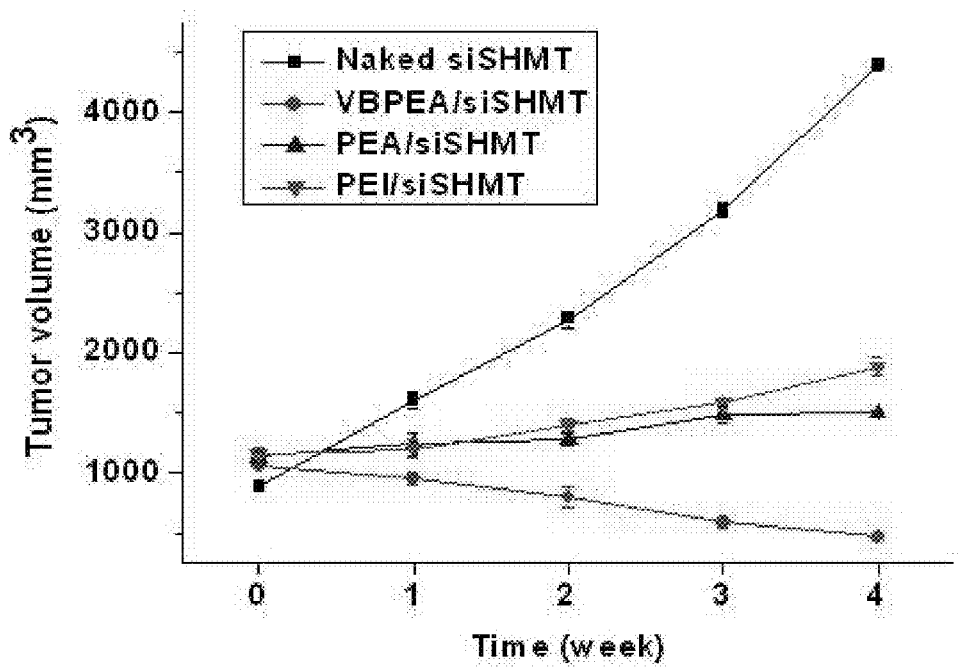
FIG. 19 shows bioluminescence images measured at one-week intervals using IVIS imaging system 100 in an in vivo experiment in a cancer-induced animal model (n=4 per group) in order to determine the change in tumor volume by siSHMT delivered by VBPEA.

As can be seen in Table 3 above and FIGS. 18 and 19, only the group administered with the VBPEA/siSHMT complex showed a substantial decrease in the tumor volume, and the tumor volume in this group significantly decreased to 50% or less of the original tumor volume.

In comparison with this, in the case in which siSHMT was delivered using the other gene carrier PEA or PEI, the rate of increase in the tumor volume significantly decreased, but the growth of the tumor was not inhibited, and in the case of the naked siSHMT-treated group administered with siSHMT alone without a gene carrier or the group treated with the VBPEA/siRNA (siScr) complex, the tumor volume increased to a level similar to that in the untreated group.

In other words, the results of the experiment in the cancer-induced animal model showed that the in vivo anticancer gene therapy using VBPEA was more efficient than the case of use of other gene carriers. In addition, it was shown that the therapeutic effect of the use of VBPEA is not a defensive level corresponding to a decrease in the tumor growth rate, but is a positive level corresponding to the removal of tumors.

Putting the above-described results together, it can be seen found that VBPEA has a significantly high gene delivery rate compared to existing gene carriers and that the complex of VBPEA with DNA has little or no cytotoxicity and shows a very high in vivo transfection efficiency. In addition, the complex of VBPEA with siRNA shows high gene silencing efficiency and can induce a high rate of cell death and the inhibition of cell proliferation in cancer cells and cancer-induced animal models, suggesting that it can be used for anticancer gene therapy.

Although the preferred embodiments of the present invention have been described for illustrative purposes, those skilled in the art will appreciate that various modifications, additions and substitutions are possible, without departing from the scope and spirit of the invention as disclosed in the accompanying claims. Pandey et al., Biomaterials 34:3716-3728, 2013, is incorporated herein in its entirety for all purposes.

The invention claimed is:

1. A gene delivery complex capable of targeting a cancer cell comprising a therapeutic gene coupled to vitamin B6-coupled poly(ester amine) (VBPEA) having the formula of Formula 1:

FORMULA 1

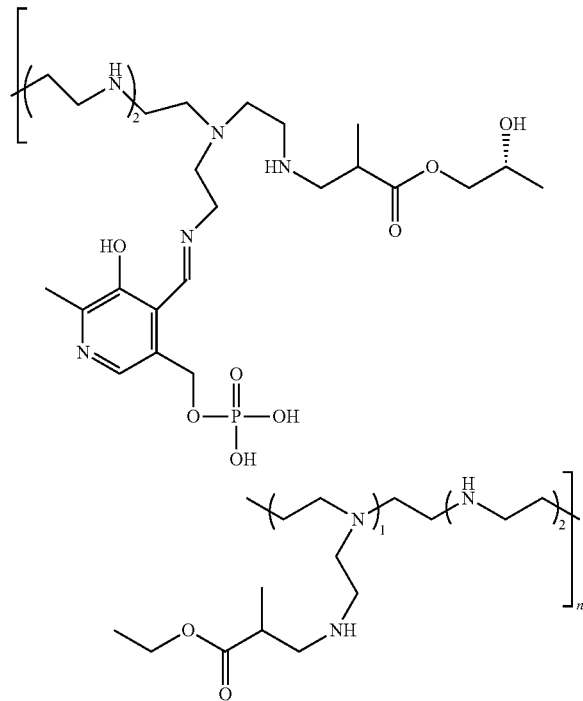

wherein n is an integer between 1 and 50,
wherein the therapeutic gene inhibits expression of serine hydroxymethyltransferase 1 (SHMT 1), and the gene delivery complex is capable of delivering the therapeutic gene to a cancer cell;

wherein the therapeutic gene and the VBPEA are coupled at a molar ratio of 1:5 to 1:40, and the therapeutic gene coupled to the VBPEA shows a zeta potential of 1 mV to 100 mV;

and wherein the therapeutic gene comprises a polynucleotide selected from the group consisting of small interfering RNAs (siRNAs), small hairpin RNAs (shRNAs), endoribonuclease-prepared siRNAs (esiRNAs), and antisense oligonucleotides.

2. The gene delivery complex of claim 1, which has an average particle size of 100 to 250 nm.

3. The gene delivery complex of claim 1, which shows a zeta potential of 25 to 50 mV.

4. A pharmaceutical formulation for gene therapy cancer treatment, comprising the gene delivery complex of claim 1 as an active ingredient.

5. The formulation of claim 4, wherein the gene delivery complex is formulated as a form for administration by inhalation or injection.

6. A method for treating cancer by administration of the pharmaceutical formulation of claim 4 to a subject in need thereof.

7. The method of claim 6, wherein the cancer is selected from the group consisting of lung cancer, bone cancer, pancreatic cancer, skin cancer, head and neck carcinoma, melanoma, uterine cancer, ovarian cancer, rectal cancer, colorectal cancer, colon cancer, breast cancer, uterine sarcoma, fallopian tube carcinoma, endometrial cancer, cervical cancer, vaginal carcinoma, vulva cancer, esophageal cancer, small intestine cancer, thyroid cancer, parathyroid cancer, soft tissue sarcoma, urethral cancer, penis cancer, prostate cancer, chronic or acute leukemia, pediatric solid tumors, differentiated lymphoma, bladder cancer, renal cancer, renal cell carcinoma, renal pelvic carcinoma, primary central nervous system lymphoma, spinal cord tumor, brain stem glioma, and pituitary adenoma.

* * * * *

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: siRNA scrambled sense

<400> SEQUENCE: 1
cguacgcgga auacuucgau u                                              21

<210> SEQ ID NO 2
<211> LENGTH: 21
<212> TYPE: RNA
<213> ORGANISM: Artificial Sequence
<220> FEATURE:
<223> OTHER INFORMATION: siRNA scrambled antisense

<400> SEQUENCE: 2
ucgaaguauu ccgcguacgu u                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA Luciferase sense

```
<400> SEQUENCE: 3
cuuacgcuga guacuucgau u                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA Luciferase antisense

<400> SEQUENCE: 4
ucgaaguacu cagcguaagu u                                              21
```